US012031149B2

(12) United States Patent
Baram et al.

(10) Patent No.: US 12,031,149 B2
(45) Date of Patent: Jul. 9, 2024

(54) COMPOSITIONS AND METHODS FOR PROMOTING GENE EDITING OF CXCR4 GENE

(71) Applicant: EmendoBio Inc.

(72) Inventors: David Baram, Tel Aviv (IL); Lior Izhar, Tel Aviv (IL); Asael Herman, Ness Ziona (IL); Rafi Emmanuel, Ramla (IL); Michal Golan Mashiach, Ness Ziona (IL); Joseph Georgeson, Rehovot (IL)

(73) Assignee: EmendoBio Inc., Wilmington, DE (US)

( * ) Notice: Subject to any disclaimer, the term of this patent is extended or adjusted under 35 U.S.C. 154(b) by 671 days.

(21) Appl. No.: 16/833,119

(22) Filed: Mar. 27, 2020

(65) Prior Publication Data
US 2023/0175020 A1 Jun. 8, 2023

Related U.S. Application Data

(60) Provisional application No. 62/824,855, filed on Mar. 27, 2019.

(51) Int. Cl.
| | |
|---|---|
| *C12N 15/00* | (2006.01) |
| *A61K 48/00* | (2006.01) |
| *A61P 37/00* | (2006.01) |
| *C12N 9/22* | (2006.01) |
| *C12N 15/11* | (2006.01) |
| *C12N 15/113* | (2010.01) |
| *C12N 15/90* | (2006.01) |

(52) U.S. Cl.
CPC ............ *C12N 15/907* (2013.01); *A61K 48/00* (2013.01); *A61P 37/00* (2018.01); *C12N 9/22* (2013.01); *C12N 15/11* (2013.01); *C12N 15/111* (2013.01); *C12N 15/1136* (2013.01); *C12N 2310/20* (2017.05); *C12N 2800/80* (2013.01)

(58) Field of Classification Search
CPC ........ C12N 15/907; C12N 9/22; C12N 15/11; C12N 15/111; C12N 15/1136; C12N 2310/20; C12N 2800/80; A61P 37/00; A61K 48/00
See application file for complete search history.

(56) References Cited

U.S. PATENT DOCUMENTS

| | | | |
|---|---|---|---|
| 2015/0071889 A1* | 3/2015 | Musunuru | C12N 15/63 435/462 |
| 2016/0251667 A1* | 9/2016 | Cigan | C12N 15/113 800/279 |
| 2018/0119123 A1* | 5/2018 | Gori | C12N 9/22 |
| 2020/0377900 A1* | 12/2020 | Cargill | C12N 15/8223 |

FOREIGN PATENT DOCUMENTS

WO WO-2009100955 A1 * 8/2009 ......... C12N 15/1138

OTHER PUBLICATIONS

Cai et al in "A Universal Approach to Correct Various HBB gene Mutations in Human Stem Cells for Gene Therapy of Beta-Thalassemia and Sickle Cell Disease" (Stem Cells Translational Medicine, 2018: vol. 7: pp. 87-97). (Year: 2018).*
Vasquez et al in "Exploiting CRISPR-Cas9 technology to investigate individual histone modifications" (Nucleic Acid Research vol. 46, No. 18, published Jun. 15, 2018; pp. 1-13). (Year: 2018).*
Wegner et al.(JBC vol. 273, No. 8, Feb. 20, 1998: pp. 4754-4760). (Year: 1998).*

* cited by examiner

*Primary Examiner* — Catherine S Hibbert
(74) *Attorney, Agent, or Firm* — Jamaica P. Szeliga; Potomac Law Group, PLLC

(57) ABSTRACT

RNA molecules comprising a guide sequence portion having 17-25 contiguous nucleotides containing nucleotides in the sequence set forth in any one of SEQ ID NOs: 1-6601 and compositions, methods, and uses thereof.

12 Claims, 1 Drawing Sheet
Specification includes a Sequence Listing.

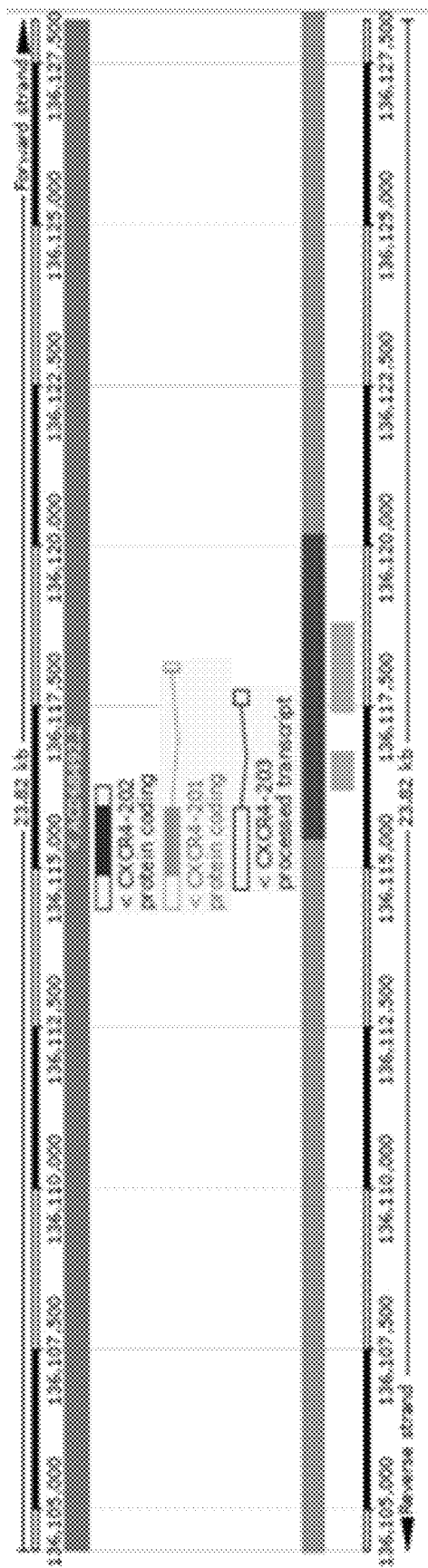

COMPOSITIONS AND METHODS FOR PROMOTING GENE EDITING OF CXCR4 GENE

This application claims the benefit of U.S. Provisional Application No. 62/824,855, filed Mar. 27, 2019, the contents of which is hereby incorporated by reference.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide sequences which are present in the file named "200327_90919-A_Sequence_Listing_AWG.txt", which is 1,302 kilobytes in size, and which was created on Mar. 26, 2020 in the IBM-PC machine format, having an operating system compatibility with MS-Windows, which is contained in the text file filed Mar. 27, 2020 as part of this application.

BACKGROUND OF INVENTION

There are several classes of DNA variation in the human genome, including insertions and deletions, differences in the copy number of repeated sequences, and single nucleotide polymorphisms (SNPs). A SNP is a DNA sequence variation occurring when a single nucleotide (adenine (A), thymine (T), cytosine (C), or guanine (G)) in the genome differs between human subjects or paired chromosomes in an individual. Over the years, the different types of DNA variations have been the focus of the research community either as markers in studies to pinpoint traits or disease causation or as potential causes of genetic disorders.

A genetic disorder is caused by one or more abnormalities in the genome. Genetic disorders may be regarded as either "dominant" or "recessive." Recessive genetic disorders are those which require two copies (i.e., two alleles) of the abnormal/defective gene to be present. In contrast, a dominant genetic disorder involves a gene or genes which exhibit(s) dominance over a normal (functional/healthy) gene or genes. As such, in dominant genetic disorders only a single copy (i.e., allele) of an abnormal gene is required to cause or contribute to the symptoms of a particular genetic disorder. Such mutations include, for example, gain-of-function mutations in which the altered gene product possesses a new molecular function or a new pattern of gene expression. Other examples include dominant negative mutations, which have a gene product that acts antagonistically to the wild-type allele.

Warts, Hypogammaglobulinemia, Infections, and Myelokathexis (WHIM) Syndrome

WHIM syndrome is an immunodeficiency disease characterized by neutropenia, hypogammaglobulinemia, and extensive human papillomavirus (HPV) infection. Heterozygous mutations in the CXCR4 gene were demonstrated to be associated with WHIM syndrome.

SUMMARY OF THE INVENTION

Disclosed is an approach for treating/preventing/ameliorating WHIM syndrome associated with heterozygous dominant mutation of the CXCR4 gene, by utilizing an RNA guided DNA nuclease to edit/correct/modify the nucleic acid sequence of a mutant allele of the CXCR4 gene such as to express a functional protein. One approach for treating the WHIM syndrome is by differential knockout of the expression of a dominant-mutant allele ("mutant allele") by disrupting the dominant-mutant allele or degrading the resulting mRNA. Another approach is by differentially repairing the mutation in the dominant-mutant allele.

The present disclosure provides a method for utilizing at least one naturally occurring heterozygous nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutant allele"), and the other allele encoding for a functional protein ("functional allele").

As used herein, the term "heterozygous single nucleotide polymorphism" or "SNP" refers to a single nucleotide position in a genome that differs between paired chromosomes within a population. As used herein the most common or most prevalent nucleotide base at the position is referred to as the reference (REF), wild-type (WT), common, or major form. Less prevalent nucleotide bases at the position are referred to as the alternative (ALT), minor, rare, or variant forms.

Embodiments of the present invention provide methods for utilizing at least one heterozygous SNP in a gene expressing a dominant mutant allele in a given cell or subject. In embodiments of the present invention, the SNP utilized may or may not be associated with a disease phenotype. In embodiments of the present invention, an RNA molecule comprising a guide sequence targets only the mutant allele of the gene by targeting the nucleotide base present at a heterozygous SNP in the mutant allele of the gene and therefore having a different nucleotide base in the functional allele of the gene.

In some embodiments, the method further comprises the step of knocking out expression of the mutated protein and allowing expression of the functional protein. In other embodiments, the method further comprises the step of correcting/editing the mutant allele, to allow expression of the functional protein.

According to embodiments of the present invention, there is provided a first RNA molecule comprising a guide sequence portion having 17-25 contiguous nucleotides containing nucleotides in the sequence set forth in any one of SEQ ID NOs: 1-6601.

According to embodiments of the present invention, there is provided a first RNA molecule comprising a guide sequence portion having 17-25 contiguous nucleotides containing nucleotides in the sequence set forth in any one of SEQ ID NOs: 1-6601.

According to some embodiments of the present invention, there is provided a composition comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided a method for inactivating a mutant CXCR4 allele in a cell, the method comprises delivering to the cell a composition comprising an RNA molecule comprising a guide sequence portion having 17-25 contiguous nucleotides containing nucleotides in the sequence set forth in any one of SEQ ID NOs: 1-6601 and a CRISPR nuclease. In some embodiments, the delivering is performed within a subject's body. In some embodiment, the delivering is performed ex-vivo. In some embodiments, the cells are HSC cell originated from the subject itself.

According to some embodiments of the present invention, there is provided a method for treating CXCR4 related WHIM syndrome, the method comprising delivering to a subject having WHIM syndrome a composition comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided use of a composition comprising an RNA molecule comprising a guide sequence portion having 17-25 contiguous nucleotides containing nucleotides in the sequence set forth in any one of SEQ ID NOs: 1-6601 and a CRISPR nuclease for inactivating a mutant CXCR4 allele in a cell, comprising delivering to the cell the composition comprising an RNA molecule comprising a guide sequence portion 17-25 contiguous nucleotides containing nucleotides in the sequence set forth in any one of SEQ ID NOs: 1-6601 and a CRISPR nuclease.

According to embodiments of the present invention, there is provided a medicament comprising an RNA molecule comprising a guide sequence portion having 17-25 contiguous nucleotides containing nucleotides in the sequence set forth in any one of SEQ ID NOs: 1-6601 and a CRISPR nuclease for use in inactivating a mutant CXCR4 allele in a cell, wherein the medicament is administered by delivering to the cell the composition comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided use of a composition comprising an RNA molecule comprising a guide sequence portion having 17-25 contiguous nucleotides containing nucleotides in the sequence set forth in any one of SEQ ID NOs: 1-6601 and a CRISPR nuclease for treating ameliorating or preventing CXCR4 related WHIM syndrome, comprising delivering to a subject having or at risk of having CXCR4 related WHIM syndrome, the composition of comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided a medicament comprising the composition comprising an RNA molecule comprising a guide sequence portion having 17-25 contiguous nucleotides containing nucleotides in the sequence set forth in any one of SEQ ID NOs: 1-6601 and a CRISPR nuclease for use in treating ameliorating or preventing WHIM syndrome, wherein the medicament is administered by delivering to a subject having or at risk of having WHIM syndrome the composition comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided a kit for inactivating a mutant CXCR4 allele in a cell, comprising an RNA molecule comprising a guide sequence portion having 17-25 contiguous nucleotides containing nucleotides in the sequence set forth in any one of SEQ ID NOs: 1-6601, a CRISPR nuclease, and/or a tracrRNA molecule; and instructions for delivering the RNA molecule; CRISPR nuclease, and/or the tracrRNA to the cell. In some embodiments, the cells are HSC cells obtained from the subject and the delivery of the composition to the cell is performed ex-vivo.

According to some embodiments of the present invention, there is provided a kit for treating CXCR4 related WHIM syndrome in a subject, comprising an RNA molecule comprising a guide sequence portion having 17-25 contiguous nucleotides containing nucleotides in the sequence set forth in any one of SEQ ID NOs: 1-6601, a CRISPR nuclease, and/or a tracrRNA molecule; and instructions for delivering the RNA molecule; CRISPR nuclease, and/or the tracrRNA to a cell of subject having or at risk of having CXCR4 related WHIM syndrome.

According to some embodiments of the present invention, there are provided cells modified by the RNA molecules, compositions, or methods of the present invention.

According to some embodiments of the present invention, there are provided cells modified by the RNA molecules, compositions, or methods of the present invention for use in treating CXCR4 related WHIM syndrome in a subject having or at risk of having CXCR4 related WHIM syndrome.

According to some embodiments of the present invention, there is provided a medicament comprising the modified cells of the present invention for treating CXCR4 related WHIM syndrome in a subject having or at risk of having CXCR4 related WHIM syndrome.

According to some embodiments of the present invention, there is provided a method for inactivating a mutant allele of the CXCR4 gene in a cell, the method comprising the steps of:
  a) selecting a cell with an CXCR4 gene mutation associated with CXCR4 related WHIM syndrome and which cell is heterozygous at one or more polymorphic sites in the CXCR4 gene selected from Table 1;
  b) introducing to the cell a composition comprising:
    a CRISPR nuclease, and
    a first RNA molecule comprising a guide sequence portion having 17-25 nucleotides,
  wherein a complex of the CRISPR nuclease and the first RNA molecule affects a double strand break in only the mutant allele of the CXCR4 gene and not in the functional allele of the CXCR4 gene in the cell;
  thereby inactivating only the mutant allele of the CXCR4 gene in the cell.

In some embodiments, the cell is a stem cell. In some embodiments, the stem cell is a hematopoietic stem/progenitor cell (HSC). In some embodiments, the delivering to the cell is performed in vitro, ex vivo, or in vivo. In some embodiments, the method is performed ex vivo and the cell is provided/explanted from an individual patient. In some embodiments, the method further comprises the step of introducing the resulting cell, with the modified/knocked out mutant CXCR4 allele, into the individual patient (e.g. autologous transplantation). In some embodiments, cells are obtained from a CXCR4 related WHIM syndrome patient, using mobilization and apheresis, or using bone marrow aspiration.

According to embodiments of the present invention, there is provided a method for inactivating a mutant allele of the CXCR4 gene in a cell, the method comprising the steps of:
  a) selecting a cell with an CXCR4 gene mutation associated with a WHIM syndrome and which cell is heterozygous at one or more polymorphic sites in the CXCR4 gene selected from Table 1;

b) introducing to the cell a composition comprising:
a CRISPR nuclease, and
a first RNA molecule comprising a guide sequence portion having 17-25 nucleotides,
wherein a complex of the CRISPR nuclease and the first RNA molecule affects a double strand break in only the mutant allele of the CXCR4 gene and not in the functional allele of the CXCR4 gene in the cell;
and wherein the method further comprises introduction of a second RNA molecule comprising a guide sequence portion capable of complexing with a CRISPR nuclease, wherein the complex of second RNA molecule and the CRISPR nuclease affects a second double strand break in the CXCR4 gene;
thereby inactivating only the mutant allele of the CXCR4 gene in the cell.

In some embodiments, the cell is heterozygous at one or more polymorphic sites in the CXCR4 gene selected from: chr:2:136875458_A_C, chr2:136875456_G_C, chr2:136875452_A_C, chr2:136875448_A_C, rs11682928, rs17848385, rs17848056, rs2471859, and rs2680880, and a complex of a first RNA molecule comprising a guide sequence portion having 17-25 nucleotides and a CRISPR nuclease affects a double strand break in only the mutant allele of the CXCR4 gene and not in the functional allele of the CXCR4 gene, and wherein a complex of the second RNA molecule and the CRISPR nuclease affects a double strand break in a non-coding region such as the 3' UTR of the CXCR4 gene.

BRIEF DESCRIPTION OF THE DRAWINGS

FIG. 1: Schematic description of CXCR4 transcripts adopted from the Ensembl database.

DETAILED DESCRIPTION

Definitions

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The terms "nucleic acid template" and "donor", refer to a nucleotide sequence that is inserted or copied into a genome. The nucleic acid template comprises a nucleotide sequence, e.g., of one or more nucleotides, that will be added to or will template a change in the target nucleic acid or may be used to modify the target sequence. A nucleic acid template sequence may be of any length, for example between 2 and 10,000 nucleotides in length, preferably between about 100 and 1,000 nucleotides in length, more preferably between about 200 and 500 nucleotides in length. A nucleic acid template may be a single stranded nucleic acid, a double stranded nucleic acid. In some embodiments, the nucleic acid template comprises a nucleotide sequence, e.g., of one or more nucleotides, that corresponds to wild type sequence of the target nucleic acid, e.g., of the target position. In some embodiments, the nucleic acid template comprises a nucleotide sequence, e.g., of one or more ribonucleotides, that corresponds to wild type sequence of the target nucleic acid, e.g., of the target position. In some embodiments, the nucleic acid template comprises modified nucleotides.

In some embodiments of the present invention, a DNA nuclease is utilized to affect a DNA break at a target site to induce cellular repair mechanisms, for example, but not limited to, non-homologous end-joining (NHEJ) or homology-directed repair (HDR). During classical NHEJ, two ends of a double-strand break (DSB) site are ligated together in a fast but also inaccurate manner (i.e. frequently resulting in mutation of the DNA at the cleavage site in the form of small insertion or deletions) whereas during HDR, an intact homologous DNA donor is used to replace the DNA surrounding the cleavage site in an accurate manner. HDR can also mediate the precise insertion of exogenous DNA at the break site. Accordingly, the term "homology-directed repair" or "HDR" refers to a mechanism for repairing DNA damage in cells, for example, during repair of double-stranded and single-stranded breaks in DNA. HDR requires nucleotide sequence homology and uses a "nucleic acid template" (nucleic acid template or donor template used interchangeably herein) to repair the sequence where the double-stranded or single break occurred (e.g., DNA target sequence). This results in the transfer of genetic information from, for example, the nucleic acid template to the DNA target sequence. HDR may result in alteration of the DNA target sequence (e.g., insertion, deletion, mutation) if the nucleic acid template sequence differs from the DNA target sequence and part or all of the nucleic acid template polynucleotide or oligonucleotide is incorporated into the DNA target sequence. In some embodiments, an entire nucleic acid template polynucleotide, a portion of the nucleic acid template polynucleotide, or a copy of the nucleic acid template is integrated at the site of the DNA target sequence.

Insertion of an exogenous sequence (also called a "donor sequence," donor template," "donor molecule" or "donor"), for example, for correction of a mutant gene or for increased expression of a wild-type gene can also be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest. A donor molecule may be any length, for example ranging from several bases e.g. 10-20 bases to multiple kilobases in length.

The donor polynucleotide can be DNA or RNA, single-stranded and/or double-stranded and can be introduced into a cell in linear or circular form. See, e.g., U.S. Patent Publication Nos. 2010/0047805; 2011/0281361; 2011/0207221; and 2019/0330620. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

Accordingly, embodiments of the present invention using a donor template for HDR may be DNA or RNA, single-stranded and/or double-stranded and can be introduced into a cell in linear or circular form. In embodiments of the present invention using: (1) a nuclease associated with an RNA molecule comprising a guide sequence to affect a double strand break in a gene prior to HDR and (2) a donor template for HDR.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to ʻcorrect' a mutated sequence in an endogenous gene (e.g., the sickle mutation in beta globin), or may be used to insert sequences with a desired purpose into an endogenous locus (e.g. a splice acceptor sequence).

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is may be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, a transgene (e.g., with or without additional coding sequences such as for the endogenous gene) is integrated into any endogenous locus, for example a safe-harbor locus, for example a CCR5 gene, a CXCR4 gene, a PPP1R12c (also known as AAVS1) gene, an albumin gene or a Rosa gene. See, e.g., U.S. Pat. Nos. 7,951,925 and 8,110,379; U.S. Publication Nos. 2008/0159996; 2010/00218264; 2010/0291048; 2012/0017290; 2011/0265198; 2013/0137104; 2013/0122591; 2013/0177983 and 2013/0177960 and U.S. Provisional Application No. 61/823,689).

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

As used herein, the term "modified cells" refers to cells in which a double strand break is affected by a complex of an RNA molecule and the CRISPR nuclease as a result of hybridization with the target sequence, i.e. on-target hybridization. The term "modified cells" may further encompass cells in which a repair or correction of a mutation was affected following the double strand break.

This invention provides a modified cell or cells obtained by use of any of the methods described herein. In an embodiment these modified cell or cells are capable of giving rise to progeny cells. In an embodiment these modified cell or cells are capable of giving rise to progeny cells after engraftment. As a non-limiting example, the modified cells may be hematopoietic stem cell (HSC), or any cell suitable for an allogenic cell transplant or autologous cell transplant.

This invention also provides a composition comprising these modified cells and a pharmaceutically acceptable carrier. Also provided is an in vitro or ex vivo method of preparing this, comprising mixing the cells with the pharmaceutically acceptable carrier.

As used herein, the term "targeting sequence" or "targeting molecule" refers a nucleotide sequence or molecule comprising a nucleotide sequence that is capable of hybridizing to a specific target sequence, e.g., the targeting sequence has a nucleotide sequence which is at least partially complementary to the sequence being targeted along the length of the targeting sequence. The targeting sequence or targeting molecule may be part of an RNA molecule that can form a complex with a CRISPR nuclease with the targeting sequence serving as the targeting portion of the CRISPR complex. When the molecule having the targeting sequence is present contemporaneously with the CRISPR molecule the RNA molecule is capable of targeting the CRISPR nuclease to the specific target sequence. Each possibility represents a separate embodiment. An RNA molecule can be custom designed to target any desired sequence.

The term "targets" as used herein, refers to a targeting sequence or targeting molecule's preferential hybridization to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

The "guide sequence portion" of an RNA molecule refers to a nucleotide sequence that is capable of hybridizing to a specific target DNA sequence, e.g., the guide sequence portion has a nucleotide sequence which is fully complementary to the DNA sequence being targeted along the length of the guide sequence portion. In some embodiments, the guide sequence portion is 17, 18, 19, 20, 21, 22, 23, 24, or 25 nucleotides in length, or approximately 17-25, 17-24, 17-22, 17-21, 18-25, 18-24, 18-23, 18-22, 18-21, 19-25, 19-24, 19-23, 19-22, 19-21, 19-20, 20-22, 18-20, 20-21, 21-22, or 17-20 nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence.

The term "non-discriminatory" as used herein refers to a guide sequence portion of an RNA molecule that targets a specific DNA sequence that is common both a mutant and functional allele of a gene.

In embodiments of the present invention, an RNA molecule comprises a guide sequence portion having 17-25 contiguous nucleotides containing nucleotides in the sequence set forth in any one of SEQ ID NOs: 1-6601. It is understood that in any of the embodiments of the present invention the guide sequence portion of an RNA molecule may comprise 17-25 contiguous nucleotides containing nucleotides in the sequence set forth in any one of SEQ ID NOs: 1-6601.

The RNA molecule and or the guide sequence portion of the RNA molecule may contain modified nucleotides. Exemplary modifications to nucleotides/polynucleotides may be synthetic and encompass polynucleotides which contain nucleotides comprising bases other than the naturally occurring adenine, cytosine, thymine, uracil, or guanine bases. Modifications to polynucleotides include polynucleotides which contain synthetic, non-naturally occurring nucleosides e.g., locked nucleic acids. Modifications to polynucleotides may be utilized to increase or decrease stability of an RNA. An example of a modified polynucleotide is an mRNA containing 1-methyl pseudouridine. For examples of modified polynucleotides and their uses, see U.S. Pat. No. 8,278,036, PCT International Publication No. WO/2015/006747, and Weissman and Kariko (2015), hereby incorporated by reference.

As used herein, "contiguous nucleotides" set forth in a SEQ ID NO refers to nucleotides in a sequence of nucleotides in the order set forth in the SEQ ID NO without any intervening nucleotides.

In embodiments of the present invention, the guide sequence portion may be 25 nucleotides in length and contain 20-22 nucleotides in the sequence set forth in any one of SEQ ID NOs: 1-6601. In embodiments of the present invention, the guide sequence portion may be less than 22 nucleotides in length. For example, in embodiments of the present invention the guide sequence portion may be 17, 18, 19, 20, or 21 nucleotides in length. In such embodiments the guide sequence portion may consist of 17, 18, 19, 20, or 21 nucleotides, respectively, in the sequence of 17-22 contiguous nucleotides set forth in any one of SEQ ID NOs: 1-6602. For example, a guide sequence portion having 17 nucleotides in the sequence of 17 contiguous nucleotides set forth in SEQ ID NO: 6602 may consist of any one of the following nucleotide sequences (nucleotides excluded from the contiguous sequence are marked in strike-through):

```
                                    (SEQ ID NO: 6602)
AAGCAUUAACCCAGUUAAAA 17 nucleotide guide sequence 1:
                                    (SEQ ID NO: 6603)
A̶A̶G̶CAUUAACCCAGUUAAAA 17 nucleotide guide sequence 2:
                                    (SEQ ID NO: 6604)
A̶A̶GCAUUAACCCAGUUAAA̶A̶

17 nucleotide guide sequence 3:
                                    (SEQ ID NO: 6605)
A̶AGCAUUAACCCAGUUAA̶A̶A̶

17 nucleotide guide sequence 4:
                                    (SEQ ID NO: 6606)
AAGCAUUAACCCAGUUA̶A̶A̶A̶
```

In embodiments of the present invention, the guide sequence portion may be greater than 20 nucleotides in length. For example, in embodiments of the present invention the guide sequence portion may be 21, 22, 23, 24 or 25 nucleotides in length. In such embodiments the guide sequence portion comprises 17-25 nucleotides in the sequence of 20, 21, or 22 contiguous nucleotides set forth in any one of SEQ ID NOs: 1-6601 and additional nucleotides fully complimentary to a nucleotide or sequence of nucleotides adjacent to the 3' end of the target sequence, 5' end of the target sequence, or both.

In embodiments of the present invention, a CRISPR nuclease and an RNA molecule comprising a guide sequence portion form a CRISPR complex that binds to a target DNA sequence to effect cleavage of the target DNA sequence. CRISPR nucleases, e.g. Cpf1, may form a CRISPR complex comprising a CRISPR nuclease and RNA molecule without a further tracrRNA molecule. Alternatively, CRISPR nucleases, e.g. Cas9, may form a CRISPR complex between the CRISPR nuclease, an RNA molecule, and a tracrRNA molecule.

In embodiments of the present invention, the RNA molecule may further comprise the sequence of a tracrRNA molecule. Such embodiments may be designed as a synthetic fusion of the guide portion of the RNA molecule and the trans-activating crRNA (tracrRNA). (See Jinek et al. Science (2012)). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base pairing and may be advantageous in certain applications of the invention described herein.

The term "tracr mate sequence" refers to a sequence sufficiently complementary to a tracrRNA molecule so as to hybridize to the tracrRNA via basepairing and promote the formation of a CRISPR complex. (See U.S. Pat. No. 8,906,616). In embodiments of the present invention, the RNA molecule may further comprise a portion having a tracr mate sequence.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Eukaryotic" cells include, but are not limited to, fungal cells (such as yeast), plant cells, animal cells, mammalian cells and human cells.

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity. Gene modification can be achieved using a nuclease, for example a CRISPR nuclease.

As used herein, the term HSC refers to both hematopoietic stem cells and hematopoietic stem progenitor cells. Non-limiting examples of stem cells include bone marrow cells, myeloid progenitor cells, a multipotent progenitor cells, a lineage restricted progenitor cells.

As used herein, "progenitor cell" refers to a lineage cell that is derived from stem cell and retains mitotic capacity and multipotency (e.g., can differentiate or develop into more than one but not all types of mature lineage of cell). As used herein "hematopoiesis" or "haemopoiesis" refers to the formation and development of various types of blood cells (e.g., red blood cells, megakaryocytes, myeloid cells (e.g., monocytes, macrophages and neutrophil), and lymphocytes) and other formed elements in the body (e.g., in the bone marrow).

The term "single nucleotide polymorphism (SNP) position", as used herein, refers to a position in which a single nucleotide DNA sequence variation occurs between members of a species, or between paired chromosomes in an individual. In the case that a SNP position exists at paired chromosomes in an individual, a SNP on one of the chromosomes is a "heterozygous SNP." The term SNP position refers to the particular nucleic acid position where a specific variation occurs and encompasses both a sequence including the variation from the most frequently occurring base at the particular nucleic acid position (also referred to as "SNP" or alternative "ALT") and a sequence including the most frequently occurring base at the particular nucleic acid position (also referred to as reference, or "REF"). Accordingly, the sequence of a SNP position may reflect a SNP (i.e. an alternative sequence variant relative to a consensus reference sequence within a population), or the reference sequence itself.

A skilled artisan will appreciate that in all of the embodiments of the present invention, each of the RNA molecules of the present invention are capable of complexing with a CRISPR nuclease such as to associate with a target genomic DNA sequence of interest next to a protospacer adjacent motif (PAM). The CRISPR nuclease then mediates cleavage of target DNA to create a double-stranded break within the protospacer. Accordingly, in embodiments of the present invention, the guide sequences and RNA molecules of the present invention may target a location 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides upstream or downstream from a PAM site In embodiments of the present invention, the guide sequences and RNA molecules of the present invention may target a location that is within the PAM site.

Therefore, in embodiments of the present invention, the RNA molecules of the present invention may affect a double strand break in an allele of a gene 1, 2, 3, 4, 5, 6, 7, 8, 9, 10, 11, 12, 13, 14, 15, 16, 17, 18, 19, 20, 21, 22, 23, 24, 25, 26, 27, 28 upstream or downstream from a polymorphic site. In further embodiments of the invention, the polymorphic site is within the PAM site. A skilled artisan will appreciate that where a heterozygous polymorphic site is present, an RNA molecule may be designed to affect a double stranded break in only the REF or ALT nucleotide base of the heterozygous polymorphic site.

In embodiments of the present invention, an RNA molecule is designed to target a heterozygous polymorphic site present in the CXCR4 gene, wherein the RNA molecule targets only the nucleotide base, REF or ALT, of the heterozygous polymorphic site present in only the mutant allele of the CXCR4 gene Embodiments The present disclosure provides a method for utilizing at least one naturally occurring nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutant allele"), and the other allele encoding for a functional protein ("functional allele"). The method further comprises the step of knocking out expression of the mutated protein and allowing expression of the functional protein. In some embodiments, the method is for treating, ameliorating, or preventing a dominant negative genetic disorder.

Embodiments of the present invention provide methods for utilizing at least one heterozygous SNP in a gene expressing a dominant mutant allele in a given cell or subject. In embodiments of the present invention, the SNP utilized may or may not be associated with a disease phenotype. In embodiments of the present invention, an RNA molecule comprising a guide sequence targets only the mutant allele of the gene by targeting the nucleotide base present at a heterozygous SNP in the mutant allele of the gene and therefore having a different nucleotide base in the functional allele of the gene.

According to embodiments of the present invention, there is provided a first RNA molecule comprising a guide sequence portion having 17-25 contiguous nucleotides containing nucleotides in the sequence set forth in any one of SEQ ID NOs: 1-6601.

According to embodiments of the present invention, there is provided a first RNA molecule comprising a guide sequence portion having 17-25 contiguous nucleotides containing nucleotides in the sequence set forth in any one of SEQ ID NOs: 1-6601.

According to embodiments of the present invention, an RNA molecule may further comprise a portion having a sequence which binds to a CRISPR nuclease.

According to embodiments of the present invention, the sequence which binds to a CRISPR nuclease is a tracrRNA sequence.

According to embodiments of the present invention, an RNA molecule may further comprise a portion having a tracr mate sequence.

According to embodiments of the present invention, an RNA molecule may further comprise one or more linker portions.

According to embodiments of the present invention, an RNA molecule may be up to 300, 290, 280, 270, 260, 250, 240, 230, 220, 210, 200, 190, 180, 170, 160, 150, 140, 130, 120, 110, or 100 nucleotides in length. Each possibility represents a separate embodiment. In embodiments of the present invention, the RNA molecule may be 17 up to 300 nucleotides in length, 100 up to 300 nucleotides in length, 150 up to 300 nucleotides in length, 200 up to 300 nucleotides in length, 100 to 200 nucleotides in length, or 150 up to 250 nucleotides in length. Each possibility represents a separate embodiment.

According to some embodiments of the present invention, there is provided a composition comprising an RNA molecule comprising a guide sequence portion having 17-25 contiguous nucleotides containing nucleotides in the sequence set forth in any one of SEQ ID NOs: 1-6601 and a CRISPR nuclease.

According to embodiments of the present invention, the composition may comprise a second RNA molecule comprising a guide sequence portion.

According to embodiments of the present invention, the guide sequence portion of the second RNA molecule comprises 17-25 contiguous nucleotides containing nucleotides in the sequence set forth in any one of SEQ ID NOs: 1-6601.

According to embodiments of the present invention, the 17-25 nucleotides of the guide sequence portion of the second RNA molecule are in a different sequence from the sequence of the guide sequence portion of the first RNA molecule.

According to embodiments of the present invention, the 17-25 nucleotides of the guide sequence portion of the second RNA molecule, when complexed with a CRISPR nuclease, target a non-coding region of the CXCR4 gene. In some embodiments, the non-coding region is the 3' UTR.

Embodiments of the present invention may comprise a tracrRNA molecule.

According to some embodiments of the present invention, there is provided a method for inactivating a mutant CXCR4 allele in a cell, the method comprising delivering to the cell a composition comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided a method for treating CXCR4 related WHIM syndrome, the method comprising delivering to a cell of a subject having CXCR4 related WHIM syndrome a composition comprising an RNA molecule comprising a guide sequence portion having 17-25 contiguous nucleotides containing nucleotides in the sequence set forth in any one of SEQ ID NOs: 1-6601 and a CRISPR nuclease.

According to embodiments of the present invention, the composition comprises a second RNA molecule comprising a guide sequence portion having 17-25 contiguous nucleotides containing nucleotides in the sequence set forth in any one of SEQ ID NOs: 1-6601.

According to embodiments of the present invention, the 17-25 nucleotides of the guide sequence portion of the second RNA molecule are in a different sequence from the sequence of the guide sequence portion of the first RNA molecule According to embodiments of the present invention, the CRISPR nuclease and the RNA molecule or RNA molecules are delivered to the subject and/or cells substantially at the same time or at different times.

According to embodiments of the present invention, the tracrRNA is delivered to the subject and/or cells substantially at the same time or at different times as the CRISPR nuclease and RNA molecule or RNA molecules.

According to embodiments of the present invention, the first RNA molecule targets a first heterozygous SNP present in an exon or promoter of the CXCR4 gene wherein the first RNA molecule targets the nucleotide base, REF or ALT, of the first SNP present in only the mutant allele of the CXCR4 gene, and wherein the second RNA molecule targets a sequence in a non-coding region present in both the mutant or functional allele of the CXCR4 gene.

According to embodiments of the present invention, there is provided a method comprising removing an exon containing a disease-causing mutation from a mutant allele, wherein the first RNA molecule or the first and the second RNA molecules target regions flanking an entire exon or a portion of the exon.

According to embodiments of the present invention, there is provided a method comprising removing multiple exons, the entire open reading frame of a gene, or removing the entire gene.

According to embodiments of the present invention, the first RNA molecule targets a first heterozygous SNP present in an exon or promoter of the CXCR4 gene, and wherein the second RNA molecule targets a second heterozygous SNP present in the same or a different exon or in an intron of the CXCR4 gene wherein the second RNA molecule targets the nucleotide base, REF or ALT, of the second SNP present in only the mutant allele of the CXCR4 gene, or the second RNA molecule targets a sequence in an intron present in both the mutant and functional allele of the CXCR4 gene.

According to embodiments of the present invention, the first RNA molecule or the first and the second RNA molecules target an alternative splicing signal sequence between an exon and an intron of a mutant allele.

According to embodiments of the present invention, the second RNA molecule targets a sequence present in both a mutant allele and a functional allele of the CXCR4 gene.

According to embodiments of the present invention, the second RNA molecule targets an intron. According to embodiments of the present invention, the second RNA molecule targets the 3' UTR.

According to embodiments of the present invention, there is provided a method comprising subjecting the mutant allele to insertion or deletion by an error prone non-homologous end joining (NHEJ) mechanism, generating a frameshift in the mutant allele's sequence.

According to embodiments of the present invention, the frameshift results in inactivation or knockout of the mutant allele.

According to embodiments of the present invention, the frameshift creates an early stop codon in the mutant allele.

According to embodiments of the present invention, the frameshift results in nonsense-mediated mRNA decay of the transcript of the mutant allele.

According to embodiments of the present invention, the inactivating or treating results in a truncated protein encoded by the mutant allele and a functional protein encoded by the functional allele.

According to some embodiments of the present invention, there is provided use of a composition comprising an RNA molecule comprising a guide sequence portion having 17-25 contiguous nucleotides containing nucleotides in the sequence set forth in any one of SEQ ID NOs: 1-6601 and a CRISPR nuclease inactivating a mutant CXCR4 allele in a cell, comprising delivering to the cell the RNA molecule comprising a guide sequence portion having 17-25 contiguous nucleotides containing nucleotides in the sequence set forth in any one of SEQ ID NOs: 1-6601 and the CRISPR nuclease.

According to embodiments of the present invention, there is provided a medicament comprising an RNA molecule comprising a guide sequence portion 17-25 contiguous nucleotides containing nucleotides in the sequence set forth in any one of SEQ ID NOs: 1-6601 and a CRISPR nuclease for use in inactivating a mutant CXCR4 allele in a cell, wherein the medicament is administered by delivering to the cell the composition comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided use of a composition comprising an RNA molecule comprising a guide sequence portion having 17-25 contiguous nucleotides containing nucleotides in the sequence set forth in any one of SEQ ID NOs: 1-6601 and a CRISPR nuclease for treating ameliorating or preventing WHIM, comprising delivering to a subject having or at risk of having WHIM the composition of comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided a medicament comprising the composition comprising an RNA molecule comprising a guide sequence portion having 17-25 contiguous nucleotides containing nucleotides in the sequence set forth in any one of SEQ ID NOs: 1-6601 and a CRISPR nuclease for use in treating ameliorating or preventing WHIM syndrome, wherein the medicament is administered by delivering to a subject having or at risk of having WHIM syndrome: the composition comprising an RNA molecule comprising a guide sequence portion having 17-25 contiguous nucleotides containing nucleotides in the sequence set forth in any one of SEQ ID NOs: 1-6601 and a CRISPR nuclease.

According to some embodiments of the present invention, there is provided a kit for inactivating a mutant CXCR4 allele in a cell, comprising an RNA molecule comprising a guide sequence portion having 17-25 contiguous nucleotides containing nucleotides in the sequence set forth in any one of SEQ ID NOs: 1-6601, a CRISPR nuclease, and/or a tracrRNA molecule; and instructions for delivering the RNA molecule; CRISPR nuclease, and/or the tracrRNA to the cell.

According to some embodiments of the present invention, there is provided a kit for treating WHIM syndrome in a subject, comprising an RNA molecule comprising a guide sequence portion having 17-25 contiguous nucleotides containing nucleotides in the sequence set forth in any one of SEQ ID NOs: 1-6601, a CRISPR nuclease, and/or a tracrRNA molecule; and instructions for delivering the RNA molecule; CRISPR nuclease, and/or the tracrRNA to a subject having or at risk of having WHIM syndrome.

The compositions and methods of the present disclosure may be utilized for treating, preventing, ameliorating, or slowing progression of WHIM syndrome.

In some embodiments, the method of deactivating a mutant allele comprises an exon skipping step comprising removing an exon containing a disease-causing mutation from the mutant allele. Removing an exon containing a disease-causing mutation in the mutant allele requires two RNA molecules which target regions flanking the entire exon or a portion of the exon. Removal of an exon containing the disease-causing mutation may be designed to eliminate the disease-causing action of the protein while allowing for expression of the remaining protein product which retains some or all of the wild-type activity. As an alternative to single exon skipping, multiple exons, the entire open reading frame or the entire gene can be excised using two RNA molecules flanking the region desired to be excised.

In some embodiments, the method of deactivating a mutant allele comprises delivering two RNA molecules to a cell, wherein one RNA molecule targets a first heterozygous SNP present in an exon or promoter of the CXCR4 gene wherein the RNA molecule targets the nucleotide base, REF or ALT, of the first SNP present in only the mutant allele of the CXCR4 gene, and wherein the other RNA molecule targets a second heterozygous SNP present in the same or a different exon or in an intron of the CXCR4 gene wherein the RNA molecule targets the nucleotide base, REF or ALT, of the second SNP present in only the mutant allele of the CXCR4 gene, or the second RNA molecule targets a sequence in an intron present in both the mutant or functional allele.

In some embodiments, an RNA molecule is used to target a CRISPR nuclease to an alternative splicing signal sequence between an exon and an intron of a mutant allele, thereby destroying the alternative splicing signal sequence in the mutant allele.

Any one of, or combination of, the above-mentioned strategies for deactivating a mutant allele may be used in the context of the invention.

Additional strategies may be used to deactivate a mutant allele. For example, in embodiments of the present invention, an RNA molecule is used to direct a CRISPR nuclease to an exon or a splice site of a mutant allele in order to create a double-stranded break (DSB), leading to insertion or deletion of nucleotides by an error-prone non-homologous end-joining (NHEJ) mechanism and formation of a frameshift mutation in the mutant allele. The frameshift mutation may result in: (1) inactivation or knockout of the mutant allele by generation of an early stop codon in the mutant allele, resulting in generation of a truncated protein; or (2) nonsense mediated mRNA decay of the transcript of the mutant allele. In further embodiments, one RNA molecule is used to direct a CRISPR nuclease to a promotor of a mutant allele.

In some embodiments, the method of deactivating a mutant allele further comprises enhancing activity of the functional protein such as by providing a protein/peptide, a nucleic acid encoding a protein/peptide, or a small molecule such as a chemical compound, capable of activating/enhancing activity of the functional protein.

According to some embodiments, the present disclosure provides an RNA molecule which binds to/associates with and/or directs the RNA guided DNA nuclease e.g., CRISPR nuclease to a sequence comprising at least one nucleotide which differs between a mutant allele and a functional allele (e.g., heterozygous SNP) of a gene of interest (i.e., a sequence of the mutant allele which is not present in the functional allele).

In some embodiments, the method comprises the steps of: contacting a mutant allele of a gene of interest with an allele-specific RNA molecule and a CRISPR nuclease e.g., a Cas9 protein, wherein the allele-specific RNA molecule and the CRISPR nuclease e.g., Cas9 associate with a nucleotide sequence of the mutant allele of the gene of interest which differs by at least one nucleotide from a nucleotide sequence of a functional allele of the gene of interest, thereby modifying or knocking-out the mutant allele.

In some embodiments, the allele-specific RNA molecule and a CRISPR nuclease is introduced to a cell encoding the gene of interest. In some embodiments, the cell encoding the gene of interest is in a mammalian subject. In some embodiments, the cell encoding the gene of interest is in a plant.

In some embodiments, the cleaved mutant allele is further subjected to insertion or deletion (indel) by an error prone non-homologous end joining (NHEJ) mechanism, generating a frameshift in the mutant allele's sequence. In some embodiments, the generated frameshift results in inactivation or knockout of the mutant allele. In some embodiments, the generated frameshift creates an early stop codon in the mutant allele and results in generation of a truncated protein. In such embodiments, the method results in the generation of a truncated protein encoded by the mutant allele and a functional protein encoded by the functional allele. In some embodiments, a frameshift generated in a mutant allele using the methods of the invention results in nonsense-mediated mRNA decay of the transcript of the mutant allele.

In some embodiments, the mutant allele is an allele of CXCR4 gene. In some embodiments, the RNA molecule targets a heterozygous SNP of the CXCR4 gene which co-exists with/is genetically linked to the mutated sequence associated with WHIM genetic disorder. In some embodiments, the RNA molecule targets a heterozygous SNP of the CXCR4 gene, wherein the heterozygosity of said SNP is highly prevalent in the population. In embodiments of the present invention, the REF nucleotide is prevalent in the mutant allele and not in the functional allele of an individual subject to be treated. In embodiments of the present invention, the ALT nucleotide is prevalent in the mutant allele and not in the functional allele of an individual subject to be treated. In some embodiments, a disease-causing mutation within a mutant CXCR4 allele is targeted.

In embodiments of the present invention, the heterozygous SNP may or may not be associated with an CXCR4 related disease phenotype. In embodiments of the present invention, the heterozygous SNP is associated with an CXCR4 related disease phenotype. In embodiments of the present invention, the SNP is not associated with an CXCR4 related disease phenotype In some embodiments, the heterozygous SNP is within an exon of the gene of interest. In such embodiments, a guide sequence portion of an RNA molecule may be designed to associate with a sequence of the exon of the gene of interest.

In some embodiments, a heterozygous SNP is within an intron or an exon of the gene of interest. In some embodiments, a heterozygous SNP is in a splice site between the intron and the exon.

A skilled artisan will appreciate that in all of the embodiments of the present invention, each of the RNA molecules of the present invention are capable of complexing with a CRISPR nuclease such as to associate with a target genomic DNA sequence of interest next to a protospacer adjacent motif (PAM). The CRISPR nuclease then mediates cleavage of target DNA to create a double-stranded break within the protospacer. Accordingly, in embodiments of the present invention, the guide sequences and RNA molecules of the present invention may target a location 1, 2, 3, 4, 5, 6, 7, 8, 9, 10, 11, 12, 13, 14, 15, 16, 17, 18, 19, 20, 21, 22, 23, 24, 25, 26, 27, or 28 nucleotides upstream or downstream from a PAM site. In embodiments of the present invention, the guide sequences and RNA molecules of the present invention may target a location that is within the PAM site.

Therefore, in embodiments of the present invention, the RNA molecules of the present invention may affect a double strand break in an allele of a gene 1, 2, 3, 4, 5, 6, 7, 8, 9, 10, 11, 12, 13, 14, 15, 16, 17, 18, 19, 20, 21, 22, 23, 24, 25, 26, 27, 28 upstream or downstream from a polymorphic site. In further embodiments of the invention, the polymorphic site is within the PAM site. A skilled artisan will appreciate that where a heterozygous polymorphic site is present, an RNA molecule may be designed to affect a double stranded break in only the REF or ALT nucleotide base of the heterozygous polymorphic site.

In embodiments of the present invention, an RNA molecule is designed to target a heterozygous polymorphic site present in the CXCR4 gene, wherein the RNA molecule targets only the nucleotide base, REF or ALT, of the heterozygous polymorphic site present in only the mutant allele of the CXCR4 gene Each possibility represents a separate embodiment of the present invention. In some embodiments, a guide sequence portion of an RNA molecule may be designed to associate with a sequence of the gene of interest which comprises the splice site.

In some embodiments, the method is utilized for treating a subject having a disease phenotype resulting from the heterozygote CXCR4 gene. In such embodiments, the method results in improvement, amelioration or prevention of the disease phenotype.

Embodiments referred to above refer to a CRISPR nuclease, RNA molecule(s), and tracrRNA being effective in a subject or cells at the same time. The CRISPR, RNA molecule(s), and tracrRNA can be delivered substantially at the same time or can be delivered at different times but have effect at the same time. For example, this includes delivering the CRISPR nuclease to the subject or cells before the RNA molecule and/or tracr RNA is substantially extant in the subject or cells.

According to embodiments of the present invention, there is provided a method for inactivating a mutant allele of the CXCR4 gene in a cell, the method comprising the steps of:

a) selecting a cell with an CXCR4 gene mutation associate with WHIM and who is heterozygous at one or more polymorphic sites in the CXCR4 gene selected from table 1;
b) introducing to the cell a composition comprising:
   a CRISPR nuclease, and
   a first RNA molecule comprising a guide sequence portion having 17-25 nucleotides,
wherein a complex of the CRISPR nuclease and the first RNA molecule affects a double strand break in only the mutant allele of the CXCR4 gene and not in the functional allele of the CXCR4 gene in the cell;
thereby inactivating only the mutant allele of the CXCR4 gene in the cell.

According to embodiments of the present invention, there is provided a method for inactivating a mutant allele of the CXCR4 gene in a cell, the method comprising the steps of:
a) selecting a cell with an CXCR4 gene mutation associated with WHIM syndrome and who is heterozygous at one or more polymorphic sites in the CXCR4 gene selected from table 1;
b) introducing to the cell a composition comprising:
   a CRISPR nuclease, and
   a first RNA molecule comprising a guide sequence portion having 17-25 nucleotides,
wherein a complex of the CRISPR nuclease and the first RNA molecule affects a double strand break in only the mutant allele of the CXCR4 gene and not in the functional allele of the CXCR4 gene in the cell;
and wherein the method further comprises introduction of a second RNA molecule comprising a guide sequence portion capable of complexing with a CRISPR nuclease, wherein the complex of the second RNA molecule and the CRISPR nuclease affects a second double strand break in the CXCR4 gene;
thereby inactivating only the mutant allele of the CXCR4 gene in the cell.

According to embodiments of the present invention, there is provided a method for inactivating a mutant allele of the CXCR4 gene in a cell with an CXCR4 gene mutation associated with WHIM syndrome and which cell is heterozygous at one or more polymorphic sites in the CXCR4 gene selected from table 1, the method comprising
introducing to the cell a composition comprising:
   a CRISPR nuclease, and
   a first RNA molecule comprising a guide sequence portion having 17-25 nucleotides,
wherein a complex of the CRISPR nuclease and the first RNA molecule affects a double strand break in only the mutant allele of the CXCR4 gene and not in the functional allele of the CXCR4 gene in the cell;
thereby inactivating only the mutant allele of the CXCR4 gene in the cell.

According to embodiments of the present invention, there is provided a method for inactivating a mutant allele of the CXCR4 gene in a cell with an CXCR4 gene mutation associated with WHIM syndrome and heterozygous at one or more polymorphic sites in the CXCR4 gene selected from table 1, the method comprising:
introducing to the cell a composition comprising:
   a CRISPR nuclease, and
   a first RNA molecule comprising a guide sequence portion having 17-25 nucleotides,
wherein a complex of the CRISPR nuclease and the first RNA molecule affects a double strand break in only the mutant allele of the CXCR4 gene and not in the functional allele of the CXCR4 gene in the cell;
and wherein the method further comprises introduction of a second RNA molecule comprising a guide sequence portion capable of complexing with a CRISPR nuclease, wherein the complex of the second RNA molecule and CRISPR nuclease affects a second double strand break in the CXCR4 gene;
thereby inactivating only the mutant allele of the CXCR4 gene in the cell.

In embodiments of the present invention, the guide sequence portion of the first RNA molecule comprises 17-25 contiguous nucleotides containing nucleotides in the sequence set forth in any one of SEQ ID NOs: 1-6601.

In embodiments of the present invention, the second double strand break is within a non-coding region of the CXCR4 gene.

In embodiments of the present invention, the non-coding region of the CXCR4 gene is intron 1, intron 2, or 3' UTR.

According to some embodiments of the present invention, there is provided a method for modifying a mutant allele of the CXCR4 gene having a mutation associated with WHIM syndrome in a cell, the method comprising
introducing to the cell a composition comprising:
   a CRISPR nuclease, and
   a first RNA molecule comprising a guide sequence portion having 17-25 nucleotides,
wherein a complex of the CRISPR nuclease and the first RNA molecule affects a double strand break in the mutant allele of the CXCR4 gene.

In some embodiments, the first RNA molecule targets the CRISPR nuclease to the mutation associated with WHIM syndrome.

In some embodiments, the CXCR4 mutation associated with WHIM syndrome is any one of c.1027G>T; c.1027G>A; c.1016_1017del; c.1013C>G; c.1013C>A; c.1006G>T; c.1003G>A; c.1000C>T; c.994G>T; c.786C>A; c.727A>C; c.704G>A; c.582G>C; c.506T>C; c.478G>A; c.458A>C; c.250G>C; c.250G>A; c.153T>A; c.16-14T>A of NM_003467.3.

In some embodiments, the guide sequence portion of the first RNA molecule comprises 17-25 contiguous nucleotides containing nucleotides in the sequence set forth in any one of SEQ ID NOs: 1-6601 that targets a mutation associated with WHIM syndrome.

In some embodiments, the method further comprises introduction of a donor molecule for homology directed repair, alteration, or replacement of the CXCR4 mutant allele.

In some embodiments, the first RNA molecule targets the CRISPR nuclease to a SNP position of the mutant allele.

In some embodiments, the SNP position is any one of rs2734871; rs2680880; rs2471859; rs1453114403; rs17848385; rs1179591969; rs11682928; rs972851766; rs1260455777; rs62160906; or rs9973445.

In some embodiments, the guide sequence portion of the first RNA molecule comprises 17-25 contiguous nucleotides containing nucleotides in the sequence set forth in any one of SEQ ID NOs: 1-6601 that targets a SNP position of the mutant allele.

In some embodiments, the SNP position is in a non-coding region of the CXCR4 mutant allele.

In some embodiments, the non-coding region is any one of a promoter region, 5' UTR, 3' UTR, or an intron.

In some embodiments, the SNP position is in the downstream intergenic region of the CXCR4 mutant allele.

In some embodiments, the SNP position contains a heterozygous SNP.

In some embodiments, the method further comprises introduction of a second RNA molecule comprising a guide sequence portion capable of complexing with a CRISPR nuclease, wherein the complex of the second RNA molecule and CRISPR nuclease affects a second double strand break in the CXCR4 gene or in the intergenic region downstream of the CXCR4 gene.

In some embodiments, the second RNA molecule comprises a non-discriminatory guide portion that targets both functional and mutant CXCR4 alleles.

In some embodiments, a portion of the CXCR4 mutant allele is excised by the first and second RNA molecules.

In some embodiments, the first RNA molecule targets a SNP position in the 3' UTR of the CXCR4 mutant allele, and the second RNA molecule comprises a non-discriminatory guide portion that targets a sequence in an intergenic region downstream of the CXCR4 gene.

In some embodiments, the first RNA molecule targets a SNP position in a intergenic region downstream of the mutant CXCR4 allele, and the second RNA molecule comprises a non-discriminatory guide portion that targets a sequence in the 3' UTR of the CXCR4 gene.

In some embodiments, the guide sequence portion of the second RNA molecule comprises 17-25 contiguous nucleotides containing nucleotides in the sequence set forth in any one of SEQ ID NOs: 1-6601 other than the sequence of the first RNA molecule.

In some embodiments, the second RNA molecule comprises a guide sequence portion that targets a sequence up to 500 basepairs from a CXCR4 polyadenylation sequence.

In some embodiments, the second RNA molecule targets a sequence up to 500 basepairs from the sequence targeted by the first RNA molecule.

According to embodiments of the present invention, there is provided a modified cell obtained by any one of the methods described herein.

According to embodiments of the present invention, there is provided a composition comprising a first RNA molecule comprising a guide sequence portion having 17-25 contiguous nucleotides containing nucleotides in the sequence set forth in any one of SEQ ID NOs 1-6601 and a CRISPR nuclease.

In some embodiments, the composition further comprises a second RNA molecule comprising a guide sequence portion having a sequence that targets a region of the CXCR4 gene or in the intergenic region downstream of the CXCR4 gene.

In some embodiments, the second RNA molecule comprises a non-discriminatory guide portion that targets both functional and mutant CXCR4 alleles.

In some embodiments, the guide sequence portion of the second RNA molecule comprises 17-25 contiguous nucleotides containing nucleotides in the sequence set forth in any one of SEQ ID NOs 1-6601 other than the sequence of guide sequence portion of the first RNA molecule.

According to embodiments of the present invention, there is provided a method for inactivating a mutant CXCR4 allele in a cell, the method comprising delivering to the cell any one of the compositions described herein.

According to embodiments of the present invention, there is provided a method for treating WHIM syndrome, the method comprising delivering to a cell of a subject having WHIM syndrome any one of the compositions described herein.

According to embodiments of the present invention, there is provided a use of any one of the compositions described herein for inactivating a mutant CXCR4 allele in a cell, comprising delivering to the cell any one of the compositions described herein.

According to embodiments of the present invention, there is provided a medicament comprising any one of the compositions described herein for use in inactivating a mutant CXCR4 allele in a cell, wherein the medicament is administered by delivering to the cell any one of the compositions described herein.

According to embodiments of the present invention, there is provided a use of any one of the compositions described herein for treating ameliorating or preventing CXCR4, comprising delivering to a cell of a subject having or at risk of having WHIM syndrome any one of the compositions described herein.

According to embodiments of the present invention, there is provided a medicament comprising any one of the compositions described herein for use in treating ameliorating or preventing WHIM syndrome, wherein the medicament is administered by delivering to a cell of a subject having or at risk of having WHIM syndrome any one of the compositions described herein.)

According to embodiments of the present invention, there is provided a kit for inactivating a mutant CXCR4 allele in a cell, comprising any one of the compositions described herein, and instructions for delivering the composition to the cell.

According to embodiments of the present invention, there is provided a kit for treating WHIM syndrome in a subject, comprising any one of the compositions described herein, and instructions for delivering the composition to the cell of a subject having or at risk of having WHIM syndrome.

Dominant Genetic Disorders

One of skill in the art will appreciate that all subjects with any type of heterozygote genetic disorder (e.g., dominant genetic disorder) may be subjected to the methods described herein. In one embodiment, the present invention may be used to target a gene involved in, associated with, or causative of dominant genetic disorders such as, for example, WHIM. In some embodiments, the dominant genetic disorder is CXCR4 related WHIM syndrome. In some embodiments, the target gene is the CXCR4 gene (Entrez Gene, gene ID No: 7852). Non-limiting examples of mutations associated with WHIM phenotype include c.1027G>T; c.1027G>A; c.1016_1017del; c.1013C>G; c.1013C>A; c.1006G>T; c.1003G>A; c.1000C>T; c.994G>T; c.786C>A; c.727A>C; c.704G>A; c.582G>C; c.506T>C; c.478G>A; c.458A>C; c.250G>C; c.250G>A; c.153T>A; c.16-14T>A of NM_003467.3.

CXCR4 editing strategies include, but are not limited to, (1) knocking out the entire mutated CXCR4 allele; (2) destabilizing the mutated CXCR4 allele; (3) an HDR strategy by targeting the 3' UTR of the CXCR4 gene with a non-discriminatory RNA guide molecule; (4) an HDR strategy to correct pathogenic CXCR4 mutations by specifically targeting the CXCR4 mutant allele; and (5) destabilizing the mutant allele by excision using a first RNA guide molecule that targets CXCR4 pathogenic mutations and a second RNA guide molecule that is non-discriminatory and targets an intergenic region downstream of the 3' UTR of both a functional and mutated CXCR4 allele.

More specifically, for CXCR4 allele specific knockout, two guide sequences may be utilized. The first guide targets SNPs located in a CXCR4 non-coding region such as a promoter, 5'UTR, intron, 3'UTR or intergenic region. The second guide may target non-coding regions located downstream or upstream to the CXCR4 coding exon, according to the location of the discriminatory SNP. For example, if the discriminatory SNP is located in the promoter, 5' UTR or intron (e.g. rs62160906, rs9973445, rs2680880, rs2471859 and rs11682928), the non-discriminatory guide may target the 3' UTR or intergenic regions located downstream to the CXCR4 gene in order to lead to excision of the coding exon.

Another optional strategy is to destabilize a mutated CXCR4 transcript by excising the 3'UTR by targeting a SNP in the downstream intergenic region of CXCR4 with a first guide and using a second, non-discriminatory guide targeting a sequence in the 3'UTR that is upstream to the polyadenylation signal. Alternatively, a first guide may target a SNP located in the intergenic region downstream of the CXCR4 3'UTR (e.g. rs2734871), and a second, non-discriminatory guide may target a sequence in the 3'UTR upstream to a polyadenylation signal.

In a general HDR strategy, a non-discriminatory gRNA may target a sequence in the 3' UTR of the CXCR4 gene that is common to all CXCR4 transcripts, preferably in a region such that the editing profile will not impair the stop codon or the polyadenylation signal. The donor may be a ssODN, ddODN (e.g. a PCR product) or a AAV-donor comprising homology arms covering the mutations region.

CRISPR Nucleases and PAM Recognition

In some embodiments, the sequence specific nuclease is selected from CRISPR nucleases, or a functional variant thereof. In some embodiments, the sequence specific nuclease is an RNA guided DNA nuclease. In such embodiments, the RNA sequence which guides the RNA guided DNA nuclease (e.g., Cpf1) binds to and/or directs the RNA guided DNA nuclease to the sequence comprising at least one nucleotide which differs between a mutant allele and its counterpart functional allele (e.g., SNP). In some embodiments, the CRISPR complex does not further comprise a tracrRNA. In a non-limiting example, in which the RNA guided DNA nuclease is a CRISPR protein, the at least one nucleotide which differs between the dominant mutant allele and the functional allele may be within the PAM site and/or proximal to the PAM site within the region that the RNA molecule is designed to hybridize to. A skilled artisan will appreciate that RNA molecules can be engineered to bind to a target of choice in a genome by commonly known methods in the art.

In embodiments of the present invention, a type II CRISPR system utilizes a mature crRNA:tracrRNA complex directs a CRISPR nuclease, e.g. Cas9, to the target DNA via Watson-Crick base-pairing between the crRNA and the protospacer on the target DNA next to the protospacer adjacent motif (PAM), an additional requirement for target recognition. The CRISPR nuclease then mediates cleavage of target DNA to create a double-stranded break within the protospacer. A skilled artisan will appreciate that each of the engineered RNA molecule of the present invention is further designed such as to associate with a target genomic DNA sequence of interest next to a protospacer adjacent motif (PAM), e.g., a PAM matching the sequence relevant for the type of CRISPR nuclease utilized, such as for a non-limiting example, NGG or NAG, wherein "N" is any nucleobase, for *Streptococcus pyogenes* Cas9 WT (Sp-CAS9); NNGRRT for *Staphylococcus aureus* (SaCas9); NNNVRYM for *Jejuni* Cas9 WT; NGAN or NGNG for SpCas9-VQR variant; NGCG for SpCas9-VRER variant; NGAG for SpCas9-EQR variant; NNNNGATT for *Neisseria meningitidis* (NmCas9); or TTTV for Cpf1. RNA molecules of the present invention are each designed to form complexes in conjunction with one or more different CRISPR nucleases and designed to target polynucleotide sequences of interest utilizing one or more different PAM sequences respective to the CRISPR nuclease utilized.

In some embodiments, an RNA-guided DNA nuclease e.g., a CRISPR nuclease, may be used to cause a DNA break, either double or single-stranded in nature, at a desired location in the genome of a cell. The most commonly used RNA-guided DNA nucleases are derived from CRISPR systems, however, other RNA-guided DNA nucleases are also contemplated for use in the genome editing compositions and methods described herein. For instance, see U.S. Patent Publication No. 2015/0211023, incorporated herein by reference.

CRISPR systems that may be used in the practice of the invention vary greatly. CRISPR systems can be a type I, a type II, or a type III system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Casl Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cul966.

In some embodiments, the RNA-guided DNA nuclease is a CRISPR nuclease derived from a type II CRISPR system (e.g., Cas9). The CRISPR nuclease may be derived from *Streptococcus pyogenes, Streptococcus thermophilus, Streptococcus* sp., *Staphylococcus aureus, Neisseria meningitidis, Treponema denticola, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium Finegoldia magna, Natranaerobius thermophilus, Pelotomaculum thermopropionicum, Acidithiobacillus caldus, Acidithiobacillus ferrooxidans, Allochromatiurn vinosum, Marinobacter* sp., *Nitrosococcus halophilus, Nitrosococcus watsoni, Pseudoalteromonas haloplanktis, Ktedonobacter racemifer, Methanohalobiurn evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina*, or any species which encodes a CRISPR nuclease with a known PAM sequence. CRISPR nucleases encoded by uncultured bacteria may also be used in the context of the invention. (See Burstein et al. Nature, 2017). Variants of CRIPSR proteins having known PAM sequences e.g., spCas9 D1135E variant, spCas9 VQR variant, spCas9 EQR variant, or spCas9 VRER variant may also be used in the context of the invention.

Thus, an RNA guided DNA nuclease of a CRISPR system, such as a Cas9 protein or modified Cas9 or homolog or ortholog of Cas9, or other RNA guided DNA nucleases belonging to other types of CRISPR systems, such as Cpf1 and its homologs and orthologs, may be used in the compositions of the present invention.

In certain embodiments, the CRIPSR nuclease may be a "functional derivative" of a naturally occurring Cas protein.

A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein.

In some embodiments, the CRISPR nuclease is Cpf1. Cpf1 is a single RNA-guided endonuclease which utilizes a T-rich protospacer-adjacent motif. Cpf1 cleaves DNA via a staggered DNA double-stranded break. Two Cpf1 enzymes from Acidaminococcus and Lachnospiraceae have been shown to carry out efficient genome-editing activity in human cells. (See Zetsche et al. (2015) Cell).

Thus, an RNA guided DNA nuclease of a Type II CRISPR System, such as a Cas9 protein or modified Cas9 or homologs, orthologues, or variants of Cas9, or other RNA guided DNA nucleases belonging to other types of CRISPR systems, such as Cpf1 and its homologs, orthologues, or variants, may be used in the present invention.

In some embodiments, the guide molecule comprises one or more chemical modifications which imparts a new or improved property (e.g., improved stability from degradation, improved hybridization energetics, or improved binding properties with an RNA guided DNA nuclease). Suitable chemical modifications include, but are not limited to: modified bases, modified sugar moieties, or modified internucleoside linkages. Non-limiting examples of suitable chemical modifications include: 4-acetylcytidine, 5-(carboxyhydroxymethyl)uridine; 2'-O-methylcytidine, 5-carboxymethylaminomethyl-2-thiouridine, 5-carboxymethylaminomethyluridine, dihydrouridine, 2'-O-methylpseudouridine, "beta, D-galactosylqueuosine", 2'-O-methylguanosine, inosine, N6-isopentenyladenosine, 1-methyladenosine, 1-methylpseudouridine, 1-methylguanosine, 1-methylinosine; "2,2-dimethylguanosine", 2-methyladenosine; 2-methylguanosine, 3-methylcytidine, 5-methylcytidine, N6-methyladenosine, 7-methylguanosine, 5-methylaminomethyluridine, 5-methoxyaminomethyl-2-thiouridine, "beta, D-mannosylqueuosine", 5-methoxycarbonylmethyl-2-thiouridine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl)N-methylcarbamoyl)threonine, uridine-5-oxyacetic acid-methylester, uridine-5-oxyacetic acid, wybutoxosine, queuosine, 2-thiocytidine, 5-methyl-2-thiouridine; 2-thiouridine, 4-thiouridine, 5-methyluridine, N-((9-beta-D-ribofuranosylpurine-6-yl)-carbamoyl)threonine, 2'-O-methyl-5-methyluridine, 2'-O-methyluridine, wybutosine, "3-(3-amino-3-carboxy-propyl)uridine, (acp3) u", 2'-O-methyl (M), 3'-phosphorothioate (MS), 3'-thioPACE (MSP), pseudouridine, or 1-methyl pseudo-uridine. Each possibility represents a separate embodiment of the present invention.

Guide Sequences which Specifically Target a Mutant Allele

A given gene may contain thousands of SNPs. Utilizing a 24 base pair target window for targeting each SNP in a gene would require hundreds of thousands of guide sequences. Any given guide sequence when utilized to target a SNP may result in degradation of the guide sequence, limited activity, no activity, or off-target effects. Accordingly, suitable guide sequences are necessary for targeting a given gene. By the present invention, a novel set of guide sequences have been identified for knocking out expression of a mutated protein, inactivating a mutant CXCR4 gene allele, and treating WHIM syndrome.

The present disclosure provides guide sequences capable of specifically targeting a mutant allele for inactivation while leaving the functional allele unmodified. The guide sequences of the present invention are designed to, and are most likely to, specifically differentiate between a mutant allele and a functional allele. Of all possible guide sequences which target a mutant allele desired to be inactivated, the specific guide sequences disclosed herein are specifically effective to function with the disclosed embodiments.

Briefly, the guide sequences may have properties as follows: (1) target a heterozygous SNP/insertion/deletion/indel with a high prevalence in the general population, in a specific ethnic population or in a patient population is above 1% and the SNP/insertion/deletion/indel heterozygosity rate in the same population is above 1%; (2) target a location of a SNP/insertion/deletion/indel proximal to a portion of the gene e.g., within 5 k bases of any portion of the gene, for example, a promoter, a UTR, an exon or an intron; and (3) target a mutant allele using an RNA molecule which targets a founder or common pathogenic mutations for the disease/gene. In some embodiments, the prevalence of the SNP/insertion/deletion/indel in the general population, in a specific ethnic population or in a patient population is above 1%, 2%, 3%, 4%, 5%, 6%, 7%, 8%, 9%, 10%, 11%, 12%, 13%, 14%, or 15% and the SNP/insertion/deletion/indel heterozygosity rate in the same population is above 1%, 2%, 3%, 4%, 5%, 6%, 7%, 8%, 9%, 10%, 11%, 12%, 13%, 14%, or 15%. Each possibility represents a separate embodiment and may be combined at will.

For each gene, according to SNP/insertion/deletion/indel any one of the following strategies may be used to deactivate the mutant allele: (1) Knockout strategy using one RNA molecule—one RNA molecule is utilized to direct a CRISPR nuclease to a mutant allele and create a double-strand break (DSB) leading to formation of a frameshift mutation in an exon or in a splice site region of the mutant allele; (2) Knockout strategy using two RNA molecules—two RNA molecules are utilized. A first RNA molecule targets a region in the promoter or an upstream region of a mutant allele and another RNA molecule targets downstream of the first RNA molecule in a promoter, exon, or intron of the mutant allele; (3) Exon(s) skipping strategy—one RNA molecule may be used to target a CRISPR nuclease to a splice site region, either at the 5'end of an intron (donor sequence) or the 3' end of an intron (acceptor sequence), in order to destroy the splice site. Alternatively, two RNA molecules may be utilized such that a first RNA molecule targets an upstream region of an exon and a second RNA molecule targets a region downstream of the first RNA molecule, thereby excising the exon(s). Based on the locations of identified SNPs/insertions/deletions/indels for each mutant allele, any one of, or a combination of, the above-mentioned methods to deactivate the mutant allele may be utilized.

When only one RNA molecule is used is that the location of the SNP is in an exon or in close proximity (e.g., within 20 basepairs) to a splice site between the intron and the exon such as exon 2. When two RNA molecules are used, the first guide sequence may target a SNPs such that the first SNP is in intron 1, and the second guide sequence targets a sequence within intron 2, or 3' UTR.

Guide sequences of the present invention may target a SNP in the upstream portion of the targeted gene, preferably upstream of the last exon of the targeted gene. Guide sequences may target a SNP upstream to exon 1, for example within the 5' untranslated region, or within the promoter or within the first 4-5 kilobases 5' of the transcription start site.

Guide sequences of the present invention may also target a SNP within close proximity (e.g., within 50 basepairs, more preferably with 20 basepairs) to a known protospacer adjacent motif (PAM) site.

Guide sequences of the present invention also may target: (1) a heterozygous SNP for the targeted gene; (2) a heterozygous SNPs upstream and downstream of the gene; (3) a SNPs with a prevalence of the SNP/insertion/deletion/indel in the general population, in a specific ethnic population, or in a patient population above 1%; (4) have a guanine-cytosine content of greater than 30% and less than 85%; (5) have no repeat of 4 or more thymine/uracil or 8 or more guanine, cytosine, or adenine; (6) having no off-target identified by off-target analysis; and (7) preferably target Exons over Introns or be upstream of a SNP rather than downstream of a SNP.

In embodiments of the present invention, the SNP may be upstream or downstream of the gene. In embodiments of the present invention, the SNP is within 4,000 base pairs upstream or downstream of the gene.

The at least one nucleotide which differs between the mutant allele and the functional allele, may be upstream, downstream or within the sequence of the disease-causing mutation of the gene of interest. The at least one nucleotide which differs between the mutant allele and the functional allele, may be within an exon or within an intron of the gene of interest. In some embodiments, the at least one nucleotide which differs between the mutant allele and the functional allele is within an exon of the gene of interest. In some embodiments, the at least one nucleotide which differs between the mutant allele and the functional allele is within an intron or an exon of the gene of interest, in close proximity to a splice site between the intron and the exon e.g., 1, 2, 3, 4, 5, 6, 7, 8, 9, 10, 11, 12, 13, 14, 15, 16, 17, 18, 19, or 20 nucleotides upstream or downstream to the splice site.

In some embodiments, the at least one nucleotide is a single nucleotide polymorphisms (SNPs). In some embodiments, each of the nucleotide variants of the SNP may be expressed in the mutant allele. In some embodiments, the SNP may be a founder or common pathogenic mutation.

Guide sequences may target a SNP which has both (1) a high prevalence in the general population e.g., above 1% in the population; and (2) a high heterozygosity rate in the population, e.g., above 1%. Guide sequences may target a SNP that is globally distributed. A SNP may be a founder or common pathogenic mutation. In some embodiments, the prevalence in the general population is above 1%, 2%, 3%, 4%, 5%, 6%, 7%, 8%, 9%, 10%, 11%, 12%, 13%, 14%, or 15%. Each possibility represents a separate embodiment. In some embodiments, the heterozygosity rate in the population is above 1%, 2%, 3%, 4%, 5%, 6%, 7%, 8%, 9%, 10%, 11%, 12%, 13%, 14%, or 15%. Each possibility represents a separate embodiment.

In some embodiments, the at least one nucleotide which differs between the mutant allele and the functional allele is linked to/co-exists with the disease-causing mutation in high prevalence in a population. In such embodiments, "high prevalence" refers to at least 92%, 93%, 94%, 95%, 96%, 97%, 98%, 99%, or 100%. Each possibility represents a separate embodiment of the present invention. In one embodiment, the at least one nucleotide which differs between the mutant allele and the functional allele, is a disease-associated mutation. In some embodiments, the SNP is highly prevalent in the population. In such embodiments, "highly prevalent" refers to at least 10%, 11%, 12%, 13%, 14%, 15%, 20%, 30%, 40%, 50%, 60%, or 70% of a population. Each possibility represents a separate embodiment of the present invention.

Guide sequences of the present invention may satisfy any one of the above criteria and are most likely to differentiate between a mutant allele from its corresponding functional allele.

In some embodiments the RNA molecule targets a heterozygous SNP present in the CXCR4 gene from the SNPs as shown in Table 1 below.

Delivery to Cells

It is understood that in the methods embodied, the RNA molecules and compositions described herein may be delivered to a target cell or subject by any suitable means. The following embodiments provide non-limiting examples of methods of delivery of the RNA molecules and composition of the present invention.

In some embodiments, RNA molecule compositions of the present invention may be targeted to any cell which contains and/or expresses a dominant negative allele, including any mammalian or plant cell. For example, in one embodiment the RNA molecule specifically targets a mutant CXCR4 allele and the target cell is a stem cell.

In some embodiments, the RNA molecule comprises a chemical modification. Non-limiting examples of suitable chemical modifications include 2'-0-methyl (M), 2'-0-methyl, 3'phosphorothioate (MS) or 2'-0-methyl, 3 Thio-PACE (MSP), pseudouridine, and 1-methyl pseudo-uridine. Each possibility represents a separate embodiment of the present invention.

Any suitable viral vector system may be used to deliver nucleic acid compositions e.g., the RNA molecule compositions of the subject invention. Conventional viral and non-viral based gene transfer methods can be used to introduce nucleic acids and target tissues. In certain embodiments, nucleic acids are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson (1992) Science 256:808-813; Nabel & Felgner (1993) TIBTECH 11:211-217; Mitani & Caskey (1993) TIBTECH 11:162-166; Dillon (1993) TIBTECH 11:167-175; Miller (1992) Nature 357:455-460; Van Brunt (1988) Biotechnology 6(10):1149-1154; Vigne (1995) Restorative Neurology and Neuroscience 8:35-36; Kremer & Perricaudet (1995) British Medical Bulletin 51(1):31-44; Haddada et al. (1995) in Current Topics in Microbiology and Immunology Doerfler and Bohm (eds.); and Yu et al. (1994) Gene Therapy 1:13-26.

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234, Sinorhizoboiummeliloti, *Mesorhizobium loti*, tobacco mosaic virus, potato virus X, cauliflower mosaic virus and cassava vein mosaic virus). (See, e.g., Chung et al. (2006) Trends Plant Sci. 11(1):1-4). Sonoporation using, e.g., the Sonitron 2000 system (Rich-Mar), can also be used for delivery of nucleic acids. Cationic-lipid mediated delivery of proteins and/or nucleic acids is also contemplated as an in vivo or in vitro delivery method. (See Zuris et al. (2015) Nat. Biotechnol. 33(1):73-80; see also Coelho et al. (2013) N. Engl. J. Med. 369, 819-829; Judge et al. (2006) Mol. Ther. 13, 494-505; and Basha et al. (2011) Mol. Ther. 19, 2186-2200).

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see, e.g., U.S. Pat. No. 6,008,336). Lipofection is described in e.g., U.S. Pat. Nos. 5,049,386, 4,946,787; and 4,897,355, and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (See, e.g., Crystal (1995) Science 270:404-410; Blaese et al. (1995) Cancer Gene Ther. 2:291-297; Behr et al. (1994) Bioconjugate Chem. 5:382-389; Remy et al. (1994) Bioconjugate Chem. 5:647-654; Gao et al. (1995) Gene Therapy 2:710-722; Ahmad et al. (1992) Cancer Res. 52:4817-4820; U.S. Pat. Nos. 4,186, 183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (See MacDiarmid et al (2009) Nature Biotechnology 27(7):643).

The use of RNA or DNA viral based systems for viral mediated delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (See, e.g., Buchschacher et al. (1992) J. Virol. 66:2731-2739; Johann et al. (1992) J. Virol. 66:1635-1640; Sommerfelt et al. (1990) Virol. 176:58-59; Wilson et al. (1989) J. Virol. 63:2374-2378; Miller et al. (1991) J. Virol. 65:2220-2224; PCT/US94/05700).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) Blood 85:3048-305; Kohn et al. (1995) Nat. Med. 1:1017-102; Malech et al. (1997) PNAS 94:22 12133-12138). PA317/pLASN was the first therapeutic vector used in a gene therapy trial. (Blaese et al. (1995). Transduction efficiencies of 50% or greater have been observed for MFG-S packaged vectors. (Ellem et al. (1997) Immunol Immunother. 44(1):10-20; Dranoff et al. (1997) Hum. Gene Ther. 1:111-2).

Packaging cells are used to form virus particles that are capable of infecting a host cell. Such cells include 293 cells, which package adenovirus, AAV, and Psi-2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) Proc. Natl. Acad. Sci. USA 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravitreal, intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid composition, and re-infused back into the subject organism (e.g., patient). Various cell types suitable for ex vivo transfection are well known to those of skill in the art (See, e.g., Freshney et al. (1994) Culture of Animal Cells, A Manual of Basic Technique, 3rd ed, and the references cited therein for a discussion of how to isolate and culture cells from patients).

Suitable cells include, but are not limited to, eukaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), perC6 cells, any plant cell (differentiated or undifferentiated), as well as insect cells such as Spodopterafugiperda (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with a guided nuclease system (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma, and TNF-alpha are known (as a non-limiting example see, Inaba et al., J. Exp. Med. 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Tad (differentiated antigen presenting cells) (as a non-limiting example see Inaba et al. (1992) J. Exp. Med. 176:1693-1702). Stem cells that have been modified may also be used in some embodiments.

Any one of the RNA molecule compositions described herein is suitable for genome editing in post-mitotic cells or any cell which is not actively dividing, e.g., arrested cells.

Vectors (e.g., retroviruses, liposomes, etc.) containing therapeutic nucleic acid compositions can also be administered directly to an organism for transduction of cells in vivo. Administration is by any of the routes normally used for introducing a molecule into ultimate contact with blood or tissue cells including, but not limited to, injection, infusion, topical application (e.g., eye drops and cream) and electroporation. Suitable methods of administering such nucleic acids are available and well known to those of skill in the art, and, although more than one route can be used to administer a particular composition, a particular route can often provide a more immediate and more effective reaction than another route. According to some embodiments, the composition is delivered via IV injection.

Vectors suitable for introduction of transgenes into immune cells (e.g., T-cells) include non-integrating lentivirus vectors. See, e.g., U U.S. Patent Publication No. 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (See, e.g., Remington's Pharmaceutical Sciences, 17th ed., 1989).

In accordance with some embodiments, there is provided an RNA molecule which binds to/associates with and/or directs the RNA guided DNA nuclease to a sequence comprising at least one nucleotide which differs between a mutant allele and a functional allele (e.g., SNP) of a gene of interest (i.e., a sequence of the mutant allele which is not present in the functional allele). The sequence may be within the disease associated mutation. The sequence may be upstream or downstream to the disease associated mutation. Any sequence difference between the mutant allele and the functional allele may be targeted by an RNA molecule of the present invention to inactivate the mutant allele, or otherwise disable its dominant disease-causing effects, while preserving the activity of the functional allele.

The disclosed compositions and methods may also be used in the manufacture of a medicament for treating dominant genetic disorders in a patient.

Mechanisms of Action for Several Embodiments Disclosed Herein

CXCR4 has several protein coding transcripts, differing in their N-terminus. The shorter transcript contains only a single exon with a promoter region located within intron 1 of the longer transcripts. Several mutations located in the C-terminal domain of CXCR4 have been associated with WHIM syndrome. Non-limiting examples of disease associated mutations include: c.1027G>T (p.Glu343Ter), c.1016_1017delCT (p.Ser339Cysfs), c.1013C>G (p.Ser338Ter), c.1003G>A (p.Gly335Ser), and c.1000C>T (p.Arg334Ter).

Without being bound by any theory or mechanism, the instant invention may be utilized to apply a CRISPR nuclease to correct or repair the mutant pathogenic CXCR4 allele and not the functional CXCR4 allele. For example, an allele specific HDR approach involves targeting a CXCR4 mutation with a discriminatory gRNA and providing a ssDON template. In another example, a general HDR strategy involves targeting the 3'UTR of the CXCR gene with a non-discriminatory gRNA, which targets a sequence transcribed in all CXCR4 transcripts, in a region that the editing profile will not impair the stop codon or the polyA signal. The donor may be a ddODN e.g. a PCR product, that comprises homology arms covering the mutations region.

Without being bound by any theory or mechanism, the instant invention may be utilized to apply a CRISPR nuclease to modify the mutant pathogenic CXCR4 allele and not the functional CXCR4 allele, such as to prevent expression of the mutant pathogenic allele or to produce a truncated non-pathogenic peptide from the mutant pathogenic allele, in order to prevent WHIM syndrome.

For an allele specific CXCR4 knockout, two guide sequences may be utilized, wherein the first guide targets one of a SNPs in intron 1 of the CXCR4 (NM 003467.3) as specified in table 1, while the second targets the 3'UTR of the CXCR4 gene.

TABLE 1

List of SNPs relevant for CXCR4 editing strategies described herein.

| RSID* | RS ID** | CXCR4 SNP Position |
|---|---|---|
| 2:136112303_G_A_ | rs2734871 | Downstream region |
| 2:136115979_A_T_ | rs2680880 | Intron_1 of 1 |
| 2:136116434_A_G | rs2471859 | Intron_1 of 1 |
| 2:136117888_A_C_ | rs1453114403 | Intron_1 of 1 |
| 2:136117122_T_G | rs17848385 | Intron_1 of 1 |
| 2:136117886_G_C_ | rs1179591969 | Intron_1 of 1 |
| 2:136117336_G_A | rs11682928 | Intron_1 of 1 |
| 2:136117878_A_C | rs972851766 | Intron_1 of 1 |
| 2:136117882_A_C_ | rs1260455777 | Intron_1 of 1 |
| 2:136120697_C_T | rs62160906 | Upstream region |
| 2:136121046_C_G_ | rs9973445 | Upstream region |
| 2:136112303_G_A | rs2734871 | Downstream region |

*Genome Reference Consortium Human GRCh38.p12 (GCA_000001405.27) Assembly date: December 2013 initial release; December 2017 patch release 12.
**The SNP details SNP ID No. ("rs number") are based on NCBI's 2018 database of Single Nucleotide Polymorphisms (dbSNP)).

According to the Gnomad database, there are healthy individuals harboring heterozygous nonsense or frameshift mutations located upstream to the region of the pathogenic mutations (FIG. 2). Therefore, large C-terminus truncation of the mutant allele may overcome the dominant effect of the mutation.

In some embodiments, particularly those targeting exon 2 of the CXCR4 gene such as rs2228014, the resultant peptide will lack a large portion of the C-terminus of the peptide and therefore the dominant effect of the mutation may be avoided.

Examples of RNA Guide Sequences which Specifically Target Mutant Alleles of CXCR4 Gene Although a large number of guide sequences can be designed to target a mutant allele, the nucleotide sequences described in Table 2 identified by SEQ ID NOs: 1-6601 below were specifically selected to effectively implement the methods set forth herein and to effectively discriminate between alleles.

Referring to columns 1-4, each of SEQ ID NOs: 1-6601 indicated in column 1 corresponds to an engineered guide sequence. The corresponding SNP details are indicated in column 3 and 4.

Table 2 shows guide sequences designed for use as described in the embodiments above to associate with different SNPs within a sequence of a mutant CXCR4 allele. Each engineered guide molecule is further designed such as to associate with a target genomic DNA sequence of interest that lies next to a protospacer adjacent motif (PAM), e.g., a PAM matching the sequence NGG or NAG, where "N" is any nucleobase. The guide sequences were designed to work in conjunction with one or more different CRISPR nucleases, including, but not limited to, e.g. SpCas9WT (PAM SEQ: NGG), SpCas9.VQR.1 (PAM SEQ: NGAN), SpCas9.VQR.2 (PAM SEQ: NGNG), SpCas9.EQR (PAM SEQ: NGAG), SpCas9.VRER (PAM SEQ: NGCG), SaCas9WT (PAM SEQ: NNGRRT), NmCas9WT (PAM SEQ: NNNNGATT), Cpf1 (PAM SEQ: TTTV), or JeCas9WT (PAM SEQ: NNNVRYM). RNA molecules of the present invention are each designed to form complexes in conjunction with one or more different CRISPR nucleases and designed to target polynucleotide sequences of interest utilizing one or more different PAM sequences respective to the CRISPR nuclease utilized.

TABLE 2

Guide sequences designed to associate with specific CXCR4 gene targets

| Target | SEQ ID NOs of 20 base guides | SEQ ID NOs of 21 base guides | SEQ ID NOs of 22 base guides |
|---|---|---|---|
| 2:136114901_C_A (c.1027G>T) | 1-46 | 47-94 | 95-144 |
| 2:136114901_C_T (c.1027G>A) | 1, 25, 27, 30-31, 38, 40, 145-183 | 71, 76-79, 86, 88, 184-224 | 107-108, 127-129, 136, 138, 225-267 |
| 2:136114910_CAG_C (c.1016_1017del) | 268-313 | 314-361 | 362-411 |
| 2:136114915_G_C (c.1013C>G) | 280, 412-456 | 319, 457-503 | 364, 504-552 |
| 2:136114915_G_T (c.1013C>A) | 280, 414, 417, 428, 430, 435, 451, 553-591 | 319, 459, 464, 474, 480, 482, 498, 592-632 | 364, 511, 521, 527, 529, 534, 548, 633-675 |
| 2:136114922_C_A (c.1006G>T) | 676-721 | 722-769 | 770-819 |
| 2:136114925_C_T (c.1003G>A) | 716, 820-864 | 736, 865-911 | 802, 912-960 |
| 2:136114928_G_A (c.1000C>T) | 830, 961-1005 | 869, 1006-1052 | 932, 1053-1101 |
| 2:136114934_C_A (c.994G>T) | 1102-1147 | 1148-1195 | 1196-1245 |
| 2:136115142_G_T (c.786C>A) | 1246-1291 | 1292-1339 | 1340-1389 |
| 2:136115201_T_G (c.727A>C) | 1390-1435 | 1436-1483 | 1484-1533 |
| 2:136115224_C_T (c.704G>A) | 1534-1579 | 1580-1627 | 1628-1677 |

TABLE 2-continued

Guide sequences designed to associate with specific CXCR4 gene targets

| Target | SEQ ID NOs of 20 base guides | SEQ ID NOs of 21 base guides | SEQ ID NOs of 22 base guides |
|---|---|---|---|
| 2:136115346_C_G (c.582G>C) | 1678-1723 | 1724-1771 | 1772-1821 |
| 2:136115422_A_G (c.506T>C) | 1822-1867 | 1868-1915 | 1916-1965 |
| 2:136115450_C_T (c.478G>A) | 1966-2011 | 2012-2059 | 2060-2109 |
| 2:136115470_T_G (c.458A>C) | 2110-2155 | 2156-2203 | 2204-2253 |
| 2:136115678_C_G (c.250G>C) | 2254-2299 | 2300-2347 | 2348-2397 |
| 2:136115678_C_T (c.250G>A) | 2257, 2260, 2262, 2268, 2273, 2282, 2286, 2398-2436 | 2302, 2304, 2307, 2309, 2315, 2329, 2340, 2437-2477 | 2350, 2352, 2355, 2363, 2371, 2385, 2390, 2478-2520 |
| 2:136115775_A_T (c.153T>A) | 2521-2566 | 2567-2614 | 2615-2664 |
| 2:136115926_A_T (c.16-14T>A) | 2665-2710 | 2711-2758 | 2759-2808 |
| 2:136112303_G_A rs2734871_REF | 2809-2854 | 2855-2902 | 2903-2952 |
| 2:136112303_G_A (rs2734871) SNP | 2809, 2821, 2826, 2828, 2835, 2842, 2845, 2953-2991 | 2864, 2867, 2869, 2874, 2876, 2883, 2893, 2992-3032 | 2908, 2913, 2916, 2923, 2932, 2942-2943, 3033-3075 |
| 2:136115979_A_T (rs2680880) REF | 3076-3077 | | 3078 |
| 2:136115979_A_T (rs2680880) SNP | 3076-3077 | | 3078 |
| 2:136116434_A_G (rs2471859) REF | 3079-3118 | 3119-3158 | 3159-3202 |
| 2:136116434_A_G (rs2471859)_SNP | 3098, 3101-3103, 3109, 3111, 3114, 3203-3241 | 3132, 3141-3143, 3149, 3151, 3154, 3242-3278 | 3174-3175, 3182, 3186-3187, 3195, 3198, 3279-3319 |
| 2:136117122_T_G_ (rs17848385) REF | 3320-3365 | 3366-3413 | 3414-3463 |
| 2:136117122_T_G (rs17848385) SNP | 3327-3328, 3338-3339, 3341, 3348, 3352, 3464-3502 | 3373, 3384, 3387, 3394-3395, 3399-3400, 3503-3543 | 3421-3422, 3433, 3436-3437, 3444, 3449, 3544-3586 |
| 2:136117336_G_A (rs11682928) REF | 3587-3630 | 3631-3665 | 3666-3707 |
| 2:136117336_G_A (rs11682928) SNP | 3587-3588, 3591, 3599, 3604, 3608, 3628, 3708-3746 | 3631-3633, 3636-3637, 3649, 3663, 3747-3787 | 3666-3668, 3672, 3676, 3687, 3689, 3788-3830 |
| 2:136117878_A_C (rs972851766) REF | 3831-3849 | 3850-3868 | 3869-3887 |
| 2:136117878_A_C (rs972851766) SNP | 3834-3835, 3837, 3845, 3849, 3888-3893 | 3853, 3855, 3857, 3864, 3868, 3894-3899 | 3869, 3871, 3873, 3875, 3877, 3900-3905 |
| 2:136117882_A_C (rs1260455777) REF | 3831-3834, 3836-3849, 3906-3913 | 3850-3863, 3865-3868, 3914-3921 | 3869-3870, 3872-3887, 3922-3929 |
| 2:136117882_A_C (rs1260455777) SNP | 3906, 3910, 3912-3913, 3930-3935 | 3914, 3919-3921, 3936-3941 | 3926-3929, 3942-3947 |
| 2:136117886_G_C (rs1179591969) REF | 3831-3834, 3836-3849, 3906-3913, 3948-3955 | 3850-3863, 3865-3868, 3914-3921, 3956-3963 | 3869-3870, 3872-3887, 3922-3929, 3964-3971 |
| 2:136117886_G_C (rs1179591969) SNP | 3951, 3953-3955, 3972-4001 | 3959, 3961-3963, 4002-4031 | 3968-3971, 4032-4061 |
| 2:136117888_A_C (rs1453114403) REF | 3831-3834, 3836-3849, 3906-3913, 3948-3955, 4062-4065 | 3850-3863, 3865-3868, 3914-3921, 3956-3963, 4066-4069 | 3869-3870, 3872-3887, 3922-3929, 3964-3971, 4070-4073 |
| 2:136117888_A_C (rs1453114403) SNP | 3953-3954, 4064-4065, 4074-4107 | 3962-3963, 4068-4069, 4108-4141 | 3970-3971, 4071, 4073, 4142-4175 |
| 2:136120697_C_T (rs62160906) REF | 4176-4217 | 4218-4259 | 4260-4303 |
| 2:136120697_C_T (rs62160906) SNP | 4199, 4201, 4212, 4304-4340 | 4240, 4252, 4254, 4341-4375 | 4271, 4284, 4296, 4376-4414 |

TABLE 2-continued

Guide sequences designed to associate with specific CXCR4 gene targets

| Target | SEQ ID NOs of 20 base guides | SEQ ID NOs of 21 base guides | SEQ ID NOs of 22 base guides |
| --- | --- | --- | --- |
| 2:136121046_C_G (rs9973445) REF | 4415-4458 | 4459-4486 | 4487-4526 |
| 2:136121046_C_G (rs9973445) SNP | 4421, 4427, 4434, 4440, 4442, 4527-4565 | 4465, 4477, 4566-4591 | 4492, 4498, 4510, 4592-4628 |
| 3' UTR (non-discrimintory) | 4629-5315 | 5316-5943 | 5944-6601 |

The indicated locations listed in column 1 of the Table 2 are based on gnomAD v3 database and UCSC Genome Browser assembly ID: hg38, Sequencing/Assembly provider ID: Genome Reference Consortium Human GRCh38.p12 (GCA_000001405.27). Assembly date: December 2013 initial release; December 2017 patch release 12.
The SNP details are indicated by the listed SNP ID Nos. ("rs numbers"), which are based on the NCBI 2018 database of Single Nucleotide Polymorphisms (dbSNP)). The indicated DNA mutations are associated with Transcript Consequence NM_003467.3.

Each embodiment disclosed herein is contemplated as being applicable to each of the other disclosed embodiment. For example, it is understood that any of the RNA molecules or compositions of the present invention may be utilized in any of the methods of the present invention.

REFERENCES

1. Ahmad and Allen (1992) "Antibody-mediated Specific Binging and Cytotoxicity of Liposome-entrapped Doxorubicin to Lung Cancer Cells in Vitro", Cancer Research 52:4817-20
2. Anderson (1992) "Human gene therapy", Science 256: 808-13
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200
4. Behr (1994) Gene transfer with synthetic cationic amphiphiles: Prospects for gene therapy", Bioconjugate Chem 5:382-89
5. Blaese (1995) "Vectors in cancer therapy: how will they deliver", Cancer Gene Ther. 2:291-97
6. Blaese et al. (1995) "T lymphocyte-directed gene therapy for ADA-SKID: initial trial results after 4 years", Science 270(5235):475-80
7. Buchschacher and Panganiban (1992) "Human immunodeficiency virus vectors for inducible expression of foreign genes", J. Virol. 66:2731-39
8. Burstein et al. (2017) "New CRISPR-Cas systems from uncultivated microbes", Nature 542:237-41
9. Chung et al. (2006) "*Agrobacterium* is not alone: gene transfer to plants by viruses and other bacteria", Trends Plant Sci. 11(1):1-4
10. Coelho et al. (2013) "Safety and Efficacy of RNAi Therapy for Transthyretin Amyloidosis", N Engl J. Med 369:819-29
11. Crystal (1995) "Transfer of genes to humans: early lessons and obstacles to success", Science 270(5235):404-10
12. Dillon (1993) "Regulation gene expression in gene therapy" Trends in Biotechnology 11(5):167-173
13. Dranoff et al. (1997) "A phase I study of vaccination with autologous, irradiated melanoma cells engineered to secrete human granulocyte macrophage colony stimulating factor", Hum. Gene Ther. 8(1):111-23
14. Dunbar et al. (1995) "Retrovirally marked CD34-enriched peripheral blood and bone marrow cells contribute to long-term engraftment after autologous transplantation", Blood 85:3048-57
15. Ellem et al. (1997) "A case report: immune responses and clinical course of the first human use of granulocyte/macrophage-colony-stimulating-factor-tranduced autologous melanoma cells for immunotherapy", Cancer Immunol Immunother 44:10-20
16. Gao and Huang (1995) "Cationic liposome-mediated gene transfer" Gene Ther. 2(10):710-22
17. Haddada et al. (1995) "Gene Therapy Using Adenovirus Vectors", in: The Molecular Repertoire of Adenoviruses III: Biology and Pathogenesis, ed. Doerfler and Bohm, pp. 297-306
18. Han et al. (1995) "Ligand-directed retro-viral targeting of human breast cancer cells", Proc Natl Acad Sci U.S.A. 92(21):9747-51
19. Inaba et al. (1992) "Generation of large numbers of dendritic cells from mouse bone marrow cultures supplemented with granulocyte/macrophage colony-stimulating factor", J Exp Med. 176(6):1693-702
20. Jinek et al. (2012) "A programmable dual-RNA-guided DNA endonuclease in adaptive bacterial immunity," Science 337(6096):816-21
21. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40
22. Judge et al. (2006) "Design of noninflammatory synthetic siRNA mediating potent gene silencing in vivo", Mol Ther. 13(3):494-505
23. Kohn et al. (1995) "Engraftment of gene-modified umbilical cord blood cells in neonates with adenosine deaminase deficiency", Nature Medicine 1:1017-23
24. Kremer and Perricaudet (1995) "Adenovirus and adeno-associated virus mediated gene transfer", Br. Med. Bull. 51(1):31-44
25. Macdiarmid et al. (2009) "Sequential treatment of drug-resistant tumors with targeted minicells containing siRNA or a cytotoxic drug", Nat Biotechnol. 27(7):643-51
26. Malech et al. (1997) "Prolonged production of NADPH oxidase-corrected granulocytes after gene therapy of chronic granulomatous disease", PNAS 94(22):12133-38
27. Miller et al. (1991) "Construction and properties of retrovirus packaging cells based on gibbon ape leukemia virus", J Virol. 65(5):2220-24

28. Miller (1992) "Human gene therapy comes of age", Nature 357:455-60
29. Mitani and Caskey (1993) "Delivering therapeutic genes—matching approach and application", Trends in Biotechnology 11(5):162-66
30. Nabel and Felgner (1993) "Direct gene transfer for immunotherapy and immunization", Trends in Biotechnology 11(5):211-15
31. Remy et al. (1994) "Gene Transfer with a Series of Lipophilic DNA-Binding Molecules", Bioconjugate Chem. 5(6):647-54
32. Sentmanat et al. (2018) "A Survey of Validation Strategies for CRISPR-Cas9 Editing", Scientific Reports 8:888, doi:10.1038/s41598-018-19441-8
33. Sommerfelt et al. (1990) "Localization of the receptor gene for type D simian retroviruses on human chromosome 19", J. Virol. 64(12):6214-20
34. Van Brunt (1988) "Molecular framing: transgenic animals as bioactors" Biotechnology 6:1149-54
35. Vigne et al. (1995) "Third-generation adenovectors for gene therapy", Restorative Neurology and Neuroscience 8(1,2): 35-36
36. Weissman and Kariko (2015) "mRNA: Fulfilling the promise of gene therapy", Molecular Therapy (9):1416-7.
37. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78
38. Yu et al. (1994) "Progress towards gene therapy for HIV infection", Gene Ther. 1(1):13-26
39. Zetsche et al. (2015) "Cpf1 is a single RNA-guided endonuclease of a class 2 CRIPSR-Cas system" Cell 163(3):759-71
40. Zuris et al. (2015) "Cationic lipid-mediated delivery of proteins enables efficient protein based genome editing in vitro and in vivo" Nat Biotechnol. 33(1):73-80 wherein a complex of the CRISPR nuclease and the second RNA molecule affects a double strand break in the 3' UTR of both the functional and mutant CXCR4 alleles, and wherein following the double strand break in the mutant allele of the CXCR4 gene and the double strand break in the 3' UTR of both the functional and mutant CXCR4 alleles, the CXCR4 gene of the cell expresses only the functional CXCR4 protein, wherein the first RNA molecule targets the CRISPR nuclease to a SNP position of the mutant allele, and wherein the SNP position is in a non-coding region of the CXCR4 mutant allele.

2. The method of claim 1, wherein the guide sequence portion of the first RNA molecule comprises 17-25 contiguous nucleotides containing nucleotides in the sequence set forth in any one of SEQ ID NOs: 3587-3830 that targets a SNP position of the mutant allele.

3. The method of claim 1, wherein the non-coding region is any one of a promoter region, 5' UTR, or an intron.

4. The method of claim 1, wherein a portion of the CXCR4 mutant allele is excised by the first and second RNA molecules.

5. The method of claim 1, wherein the first RNA molecule targets a SNP position in an intron of the mutant CXCR4 allele.

6. The method of claim 1, wherein the guide sequence portion of the second RNA molecule comprises 17-25 contiguous nucleotides containing nucleotides in the sequence set forth in any one of SEQ ID NOs: 4629-6601.

7. The method of claim 1, wherein the second RNA molecule comprises a guide sequence portion that targets a sequence up to 500 basepairs from a CXCR4 polyadenylation sequence.

SEQUENCE LISTING

The patent contains a lengthy sequence listing. A copy of the sequence listing is available in electronic form from the USPTO web site (https://seqdata.uspto.gov/?pageRequest=docDetail&DocID=US12031149B2). An electronic copy of the sequence listing will also be available from the USPTO upon request and payment of the fee set forth in 37 CFR 1.19(b)(3).

The invention claimed is:

1. A method for modifying a mutant allele of the CXCR4 gene having a mutation associated with wart, hypogammaglobulinemia, infection, and myelokathexis (WHIM) syndrome in a cell without knocking out the expression of a functional CXCR4 protein encoded by a functional allele of the CXCR4 gene, the method comprising introducing to the cell a composition comprising:

a CRISPR nuclease, and a first RNA molecule comprising a guide sequence portion having 17-25 nucleotides, and a second RNA molecule comprising a non-discriminatory guide sequence portion having 17-25 nucleotides, wherein a complex of the CRISPR nuclease and the first RNA molecule affects a double strand break in the mutant allele of the CXCR4 gene but not the functional CXCR4 allele, 8. The method of claim 1, wherein the first RNA molecule further comprises a guide sequence portion comprising 17-22 continuous nucleotides containing nucleotides in the sequence set forth in SEQ ID NO: 3815.

9. The method of claim 8, wherein a portion of the CXCR4 mutant allele is excised by the first and second RNA molecules.

10. The method of claim 8, wherein the guide sequence portion of the second RNA molecule comprises 17-25 contiguous nucleotides containing nucleotides in the sequence set forth in any one of SEQ ID NOs: 4629-6601.

11. The method of claim 8, wherein the guide sequence portion of the second RNA molecule comprises 17-22 contiguous nucleotides containing nucleotides in the sequence set forth in SEQ ID NO: 4629-6601.

12. The method of claim 8, wherein the second RNA molecule comprises a guide sequence portion that targets a sequence up to 500 basepairs from a CXCR4 polyadenylation sequence.

* * * * *